US008557555B2

(12) United States Patent
Haefner et al.

(10) Patent No.: US 8,557,555 B2
(45) Date of Patent: Oct. 15, 2013

(54) SYNTHETIC PHYTASE VARIANTS

(71) Applicant: BASF SE, Ludwigshafen (DE)

(72) Inventors: Stefan Haefner, Speyer (DE); Annegret Welzel, Ludwigshafen (DE); Robert Thummer, Mannheim (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/689,958

(22) Filed: Nov. 30, 2012

(65) Prior Publication Data

US 2013/0108738 A1    May 2, 2013

Related U.S. Application Data

(63) Continuation of application No. PCT/IB2012/051933, filed on Apr. 18, 2012.

(60) Provisional application No. 61/477,637, filed on Apr. 21, 2011.

(30) Foreign Application Priority Data

Apr. 21, 2011   (EP) .................................... 11163410

(51) Int. Cl.
| | | |
|---|---|---|
| *C12N 9/00* | (2006.01) | |
| *C12N 9/16* | (2006.01) | |
| *C12N 1/20* | (2006.01) | |
| *C12N 15/00* | (2006.01) | |
| *C07H 21/04* | (2006.01) | |

(52) U.S. Cl.
USPC ..... 435/196; 435/183; 435/252.3; 435/320.1; 536/23.2

(58) Field of Classification Search
None
See application file for complete search history.

(56) References Cited

U.S. PATENT DOCUMENTS

| 2008/0263688 A1 | 10/2008 | Lassen et al. |
| 2008/0299622 A1 | 12/2008 | Paulson et al. |
| 2012/0201923 A1 | 8/2012 | Haefner et al. |

FOREIGN PATENT DOCUMENTS

| EP | 0 420 358 B1 | 5/1999 |
| WO | WO-02/48332 A2 | 6/2002 |
| WO | WO-2006/038062 A1 | 4/2006 |
| WO | WO-2006/043178 A2 | 4/2006 |
| WO | WO-2007/112739 A1 | 10/2007 |
| WO | WO-2007/128160 A1 | 11/2007 |
| WO | WO-2008/092901 A2 | 8/2008 |
| WO | WO-2008/097619 A2 | 8/2008 |
| WO | WO-2008/097620 A1 | 8/2008 |
| WO | WO-2008/116878 A1 | 10/2008 |
| WO | WO-2010/034835 A2 | 1/2010 |
| WO | WO-2011/048046 A2 | 4/2011 |

OTHER PUBLICATIONS

Chica et al. Curr Opin Biotechnol. Aug. 2005;16(4):378-84.*
Sen et al. Appl Biochem Biotechnol. Dec. 2007;143(3):212-23.*
Amerah, A. M., et al., "Influence of Feed Processing on the Efficacy of Exogenous Enzymes in Broiler Diets", World's Poultry Science Journal, vol. 67, (2011), pp. 29-45.
Haefner, S., et al., "Biotechnological Production and Applications of Phytases", Appl. Microbiol Biotechnol, vol. 68, (2005), pp. 588-597.
Zinin, N. V., et al., "Gene Cloning, Expression and Characterization of Novel Phytase from *Obesumbacterium proteus*", FEMS Microbiology Letters, vol. 236, (2004), pp. 283-290.
Notification of Transmittal of the International Search Report and the Written Opinion of the International Searching Aughority, or the Declaration dated Aug. 10, 2012.
International Search Report PCT/IB12/51933 dated Aug. 10, 2012.

* cited by examiner

*Primary Examiner* — Christian Fronda
(74) *Attorney, Agent, or Firm* — Novak Druce Connolly Bove + Quigg LLP

(57) ABSTRACT

The invention relates to a synthetic phytase with elevated thermostability, elevated stability to acids at pH 2, elevated stability to pepsin and with a broadened active pH range, and to an isolated nucleic acid sequence coding for a synthetic phytase and to the use of the phytase in an animal feed for reducing the phosphate content in the slurry and to animal feed additives and animal feeds comprising the synthetic phytase.

10 Claims, 7 Drawing Sheets

SEQUENCE LISTING

```
<160> NUMBER OF SEQ ID NOS: 26

<210> SEQ ID NO 1
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 1
gayccnytnt tycaycc                                                    17

<210> SEQ ID NO 2
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 2
```

```
ggngtrttrt cnggytg                                                17
```

<210> SEQ ID NO 3
<211> LENGTH: 17
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (9)..(9)
<223> OTHER INFORMATION: n is a, c, g, or t

<400> SEQUENCE: 3

```
gcdatrttng trtcrtg                                                17
```

<210> SEQ ID NO 4
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 4

```
wcagntgwtn gtnctg                                                 16
```

<210> SEQ ID NO 5
<211> LENGTH: 26
<212> TYPE: DNA
<213> ORGANISM: Artificial Sequence
<220> FEATURE:
<223> OTHER INFORMATION: Primer

<400> SEQUENCE: 5

```
cttcgagagc cactttatta ccgtcg                                      26
```

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6

```
ccaatgttgt gctgctgaca atagg                                       25
```

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7

```
ccgaactcat cagcgctaaa gatgc                                       25
```

```
<210> SEQ ID NO 8
<211> LENGTH: 16
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (8)..(8)
<223> OTHER INFORMATION: n is a, c, g, or t

<400> SEQUENCE: 8
cawcgwcnga sasgaa                                                    16

<210> SEQ ID NO 9
<211> LENGTH: 26
<212> TYPE: DNA
<213> ORGANISM: Artificial Sequence
<220> FEATURE:
<223> OTHER INFORMATION: Primer

<400> SEQUENCE: 9
cgcagtttga cttgatgtcg cgcacg                                         26

<210> SEQ ID NO 10
<211> LENGTH: 26
<212> TYPE: DNA
<213> ORGANISM: Artificial Sequence
<220> FEATURE:
<223> OTHER INFORMATION: Primer

<400> SEQUENCE: 10
gtcgcgcacg ccctatatcg ccaagc                                         26

<210> SEQ ID NO 11
<211> LENGTH: 25
<212> TYPE: DNA
<213> ORGANISM: Artificial Sequence
<220> FEATURE:
<223> OTHER INFORMATION: Primer

<400> SEQUENCE: 11
ctgcaaacca tcgcacacgc actgg                                          25

<210> SEQ ID NO 12
<211> LENGTH: 1341
<212> TYPE: DNA
<213> ORGANISM: Hafnia sp.
<220> FEATURE:
<221> NAME/KEY: sig_peptide
<222> LOCATION: (1)..(99)

<400> SEQUENCE: 12
atgacaatct ctctgtttaa ccgtaataaa cccgctattg cacagcgtat tttatgtcct     60
ctgatcgtgg ctttattctc aggtttaccg gcatacgcca gtgataccgc ccctgctggg    120
ttccagttgg aaaaggttgt tatcctaagc agacatggcg tacgcgcgcc aaccaaaatg    180
acacaaacga tgcgcaacgt cacacctcac cagtggcctg aatggccggt aaaactcggc    240
tatatcacgc cccgcggtga acatctgatt agcctgatgg gcggttttta tcgagagcgc    300
tttcagcaac aaggcttatt acctaaggat aactgtccta caccagatgc cgtgtatgtt    360
tgggcagacg tcgatcaacg cacacgtaaa accggcgagg ccttcttagc gggtcttgct    420
ccccagtgtg atttagcgat ccaccatcag caaaacattc agcaggccga tccgctgttc    480
catcctgtga aagccggtat ctgttcgatg gataaatcac aggcacacgc cgccgttgaa    540
```

-continued

```
aagcaggcag gcacaccgat tgagacgctc aatcaacgct atcaagcatc tttagcgctg      600
atgagttcgg tactcgattt tccaaaatcc ccctattgtc agcagcacaa cattggcaaa      660
ctctgcgatt tttcacaggc gatgcctagc aggctggcga taaatgacga cggtaataaa      720
gtggctctcg aaggtgccgt gggactttca tcgacgttgg ctgaaatttt cctgctggaa      780
cacgctcagg gaatgcctaa agtggcttgg gggaatattc acactgagca gcaatgggac      840
tctctgttaa aattgcataa tgcgcagttt gacttgatgt cgcgcacgcc ctatatcgcc      900
aagcataacg gtactccact gctgcaaacc atcgcacacg cactgggttc aatatcgcg       960 agtcgcccac tgccggatat ttcgccagac aataagatcc tgtttattgc cggtcacgac     1020
accaatattg ccaatatttc tggcatgcta gggatgacat ggacacttcc gggacagcca     1080
gataacacgc ctccgggcgg ggctttagtg tttgaacgtt gggtagataa cgcggggaaa     1140
ccgtatgtta gcgtgaatat ggtgtatcaa acactggcac agttgcacga ccagacgccg     1200
ctaacgttgc agcatcctgc gggcagcgta cgactaaaca taccgggttg cagcgatcaa     1260
acgcccgatg gctattgccc gctctccacc ttcagccgtt tagtcaacca cagcgttgag     1320
cctgcgtgcc agcttcctta a                                              1341
```

<210> SEQ ID NO 13
<211> LENGTH: 446
<212> TYPE: PRT
<213> ORGANISM: Hafnia sp.
<220> FEATURE:
<221> NAME/KEY: SIGNAL
<222> LOCATION: (1)..(33)

<400> SEQUENCE: 13

```
Met Thr Ile Ser Leu Phe Asn Arg Asn Lys Pro Ala Ile Ala Gln Arg
1               5                   10                  15

Ile Leu Cys Pro Leu Ile Val Ala Leu Phe Ser Gly Leu Pro Ala Tyr
            20                  25                  30

Ala Ser Asp Thr Ala Pro Ala Gly Phe Gln Leu Glu Lys Val Val Ile
        35                  40                  45

Leu Ser Arg His Gly Val Arg Ala Pro Thr Lys Met Thr Gln Thr Met
    50                  55                  60

Arg Asn Val Thr Pro His Gln Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Glu Arg Phe Gln Gln Gln Gly Leu Leu Pro Lys Asp Asn Cys
            100                 105                 110

Pro Thr Pro Asp Ala Val Tyr Val Trp Ala Asp Val Asp Gln Arg Thr
        115                 120                 125

Arg Lys Thr Gly Glu Ala Phe Leu Ala Gly Leu Ala Pro Gln Cys Asp
    130                 135                 140

Leu Ala Ile His His Gln Gln Asn Ile Gln Gln Ala Asp Pro Leu Phe
145                 150                 155                 160

His Pro Val Lys Ala Gly Ile Cys Ser Met Asp Lys Ser Gln Ala His
                165                 170                 175

Ala Ala Val Glu Lys Gln Ala Gly Thr Pro Ile Glu Thr Leu Asn Gln
            180                 185                 190

Arg Tyr Gln Ala Ser Leu Ala Leu Met Ser Ser Val Leu Asp Phe Pro
        195                 200                 205

Lys Ser Pro Tyr Cys Gln Gln His Asn Ile Gly Lys Leu Cys Asp Phe
    210                 215                 220
```

Ser Gln Ala Met Pro Ser Arg Leu Ala Ile Asn Asp Asp Gly Asn Lys
225                 230                 235                 240

Val Ala Leu Glu Gly Ala Val Gly Leu Ser Ser Thr Leu Ala Glu Ile
            245                 250                 255

Phe Leu Leu Glu His Ala Gln Gly Met Pro Lys Val Ala Trp Gly Asn
                260                 265                 270

Ile His Thr Glu Gln Gln Trp Asp Ser Leu Lys Leu His Asn Ala
        275                 280                 285

Gln Phe Asp Leu Met Ser Arg Thr Pro Tyr Ile Ala Lys His Asn Gly
    290                 295                 300

Thr Pro Leu Leu Gln Thr Ile Ala His Ala Leu Gly Ser Asn Ile Ala
305                 310                 315                 320

Ser Arg Pro Leu Pro Asp Ile Ser Pro Asp Asn Lys Ile Leu Phe Ile
                325                 330                 335

Ala Gly His Asp Thr Asn Ile Ala Asn Ile Ser Gly Met Leu Gly Met
                340                 345                 350

Thr Trp Thr Leu Pro Gly Gln Pro Asp Asn Thr Pro Pro Gly Gly Ala
        355                 360                 365

Leu Val Phe Glu Arg Trp Val Asp Asn Ala Gly Lys Pro Tyr Val Ser
370                 375                 380

Val Asn Met Val Tyr Gln Thr Leu Ala Gln Leu His Asp Gln Thr Pro
385                 390                 395                 400

Leu Thr Leu Gln His Pro Ala Gly Ser Val Arg Leu Asn Ile Pro Gly
                405                 410                 415

Cys Ser Asp Gln Thr Pro Asp Gly Tyr Cys Pro Leu Ser Thr Phe Ser
                420                 425                 430

Arg Leu Val Asn His Ser Val Glu Pro Ala Cys Gln Leu Pro
        435                 440                 445

<210> SEQ ID NO 14
<211> LENGTH: 1074
<212> TYPE: DNA
<213> ORGANISM: Hafnia sp.

<400> SEQUENCE: 14
atgacaatct ctctgtttaa ccgtaataaa cccgctattg cacagcgtat tttatgtcct     60
ctgatcgtgg ctttattctc aggtttaccg gcatacgcca gtgataccgc ccctgctggg    120
ttccagttgg aaaaggttgt tatcctaagc agacatggcg tacgcgcgcc aaccaaaatg    180
acacaaacga tgcgcaacgt cacacctcac cagtggcctg aatggccggt aaaactcggc    240
tatatcacgc cccgcggtga acatctgatt agcctgatgg gcggttttta tcgagagcgc    300
tttcagcaac aaggcttatt acctaaggat aactgtccta caccagatgc cgtgtatgtt    360
tgggcagacg tcgatcaacg cacacgtaaa accggcgagg ccttcttagc gggtcttgct    420
ccccagtgtg atttagcgat ccaccatcag caaaacattc agcaggccga tccgctgttc    480
catcctgtga agccggtat ctgttcgatg gataaatcac aggcacacgc cgccgttgaa    540
aagcaggcag gcacaccgat tgagacgctc aatcaacgct atcaagcatc tttagcgctg    600
atgagttcgg tactcgattt tccaaaatcc cctattgtc agcagcacaa cattggcaaa    660
ctctgcgatt tttcacaggc gatgcctagc aggctggcga taatgacga cggtaataaa    720 gtggctctcg aaggtgccgt gggactttca tcgacgttgg ctgaaatttt cctgctggaa    780
cacgctcagg gaatgcctaa agtggcttgg gggaatattc acactgagca gcaatgggac    840
tctctgttaa aattgcataa tgcgcagttt gacttgatgt cgcgcacgcc ctatatcgcc    900

```
aagcataacg gtactccact gctgcaaacc atcgcacacg cactgggttc caatatcgcg    960
agtcgcccac tgccggatat ttcgccagac aataagatcc tgtttattgc cggtcacgac   1020
accaatattg ccaatatttc tggcatgcta gggatgacat ggacacttcc ggga         1074
```

```
<210> SEQ ID NO 15
<211> LENGTH: 270
<212> TYPE: DNA
<213> ORGANISM: Yersinia mollaretii

<400> SEQUENCE: 15
cagcccgata acaccccgcc gggtgggggg ctggtgtttg aactatggca gaatccagat     60
aaccatcagc aatatgtcgc agttaagatg ttctatcaaa caatggatca gttacgaaat    120
agtgaaaagt tagacctgaa aagtcatcca gccggtattg ttcccattga gatcgaaggt    180
tgtgagaaca tcggtacaga caaactttgc cagcttgata ccttccaaaa gagagtggct    240
caggtgattg aacctgcatg ccatatttaa                                     270
```

```
<210> SEQ ID NO 16
<211> LENGTH: 1344
<212> TYPE: DNA
<213> ORGANISM: Artificial Sequence
<220> FEATURE:
<223> OTHER INFORMATION: synthetic construct
<220> FEATURE:
<221> NAME/KEY: sig_peptide
<222> LOCATION: (1)..(99)

<400> SEQUENCE: 16
atgacaatct ctctgtttaa ccgtaataaa cccgctattg cacagcgtat tttatgtcct     60
ctgatcgtgg ctttattctc aggtttaccg gcatacgcca gtgataccgc ccctgctggg    120
ttccagttgg aaaaggttgt tatcctaagc agacatggcg tacgcgcgcc aaccaaaatg    180
acacaaacga tgcgcaacgt cacacctcac cagtggcctg aatggccggt aaaactcggc    240
tatatcacgc cccgcggtga acatctgatt agcctgatgg gcggttttta tcgagagcgc    300
tttcagcaac aaggcttatt acctaaggat aactgtccta caccagatgc cgtgtatgtt    360
tgggcagacg tcgatcaacg cacacgtaaa accggcgagg ccttcttagc gggtcttgct    420
ccccagtgtg atttagcgat ccaccatcag caaaacattc agcaggccga tccgctgttc    480
catcctgtga aagccggtat ctgttcgatg gataaatcac aggcacacgc cgccgttgaa    540
aagcaggcag gcacaccgat tgagacgctc aatcaacgct atcaagcatc tttagcgctg    600
atgagttcgg tactcgattt tccaaaatcc cctattgtc agcagcacaa cattggcaaa    660
ctctgcgatt tttcacaggc gatgcctagc aggctggcga taaatgacga cggtaataaa    720
gtggctctcg aaggtgccgt gggactttca tcgacgttgg ctgaaatttt cctgctggaa    780
cacgctcagg gaatgcctaa agtggcttgg ggaatattc acactgagca gcaatgggac    840
tctctgttaa aattgcataa tgcgcagttt gacttgatgt cgcgcacgcc ctatatcgcc    900
aagcataacg gtactccact gctgcaaacc atcgcacacg cactgggttc caatatcgcg    960
agtcgcccac tgccggatat ttcgccagac aataagatcc tgtttattgc cggtcacgac   1020
accaatattg ccaatatttc tggcatgcta gggatgacat ggacacttcc gggacagccc   1080
gataacaccc cgccgggtgg ggggctggtg tttgaactat ggcagaatcc agataaccat   1140
cagcaatatg tcgcagttaa gatgttctat caaacaatgg atcagttacg aaatagtgaa   1200
aagttagacc tgaaaagtca tccagccggt attgttccca ttgagatcga aggttgtgag   1260
```
aacatcggta cagacaaact tgccagctt gataccttcc aaaagagagt ggctcaggtg    1320
attgaacctg catgccatat ttaa                                         1344

<210> SEQ ID NO 17
<211> LENGTH: 447
<212> TYPE: PRT
<213> ORGANISM: Artificial Sequence
<220> FEATURE:
<223> OTHER INFORMATION: synthetic construct
<220> FEATURE:
<221> NAME/KEY: SIGNAL
<222> LOCATION: (1)..(33)

<400> SEQUENCE: 17

```
Met Thr Ile Ser Leu Phe Asn Arg Asn Lys Pro Ala Ile Ala Gln Arg
1               5                   10                  15

Ile Leu Cys Pro Leu Ile Val Ala Leu Phe Ser Gly Leu Pro Ala Tyr
            20                  25                  30

Ala Ser Asp Thr Ala Pro Ala Gly Phe Gln Leu Glu Lys Val Val Ile
        35                  40                  45

Leu Ser Arg His Gly Val Arg Ala Pro Thr Lys Met Thr Gln Thr Met
50                  55                  60

Arg Asn Val Thr Pro His Gln Trp Pro Glu Trp Pro Val Lys Leu Gly
65                  70                  75                  80

Tyr Ile Thr Pro Arg Gly Glu His Leu Ile Ser Leu Met Gly Gly Phe
                85                  90                  95

Tyr Arg Glu Arg Phe Gln Gln Gln Gly Leu Leu Pro Lys Asp Asn Cys
            100                 105                 110

Pro Thr Pro Asp Ala Val Tyr Val Trp Ala Asp Val Asp Gln Arg Thr
        115                 120                 125

Arg Lys Thr Gly Glu Ala Phe Leu Ala Gly Leu Ala Pro Gln Cys Asp
130                 135                 140

Leu Ala Ile His His Gln Gln Asn Ile Gln Gln Ala Asp Pro Leu Phe
145                 150                 155                 160

His Pro Val Lys Ala Gly Ile Cys Ser Met Asp Lys Ser Gln Ala His
                165                 170                 175

Ala Ala Val Glu Lys Gln Ala Gly Thr Pro Ile Glu Thr Leu Asn Gln
            180                 185                 190

Arg Tyr Gln Ala Ser Leu Ala Leu Met Ser Ser Val Leu Asp Phe Pro
        195                 200                 205

Lys Ser Pro Tyr Cys Gln His Asn Ile Gly Lys Leu Cys Asp Phe
210                 215                 220

Ser Gln Ala Met Pro Ser Arg Leu Ala Ile Asn Asp Asp Gly Asn Lys
225                 230                 235                 240

Val Ala Leu Glu Gly Ala Val Gly Leu Ser Ser Thr Leu Ala Glu Ile
                245                 250                 255

Phe Leu Leu Glu His Ala Gln Gly Met Pro Lys Val Ala Trp Gly Asn
            260                 265                 270

Ile His Thr Glu Gln Gln Trp Asp Ser Leu Leu Lys Leu His Asn Ala
        275                 280                 285

Gln Phe Asp Leu Met Ser Arg Thr Pro Tyr Ile Ala Lys His Asn Gly
    290                 295                 300

Thr Pro Leu Leu Gln Thr Ile Ala His Ala Leu Gly Ser Asn Ile Ala
305                 310                 315                 320

Ser Arg Pro Leu Pro Asp Ile Ser Pro Asp Asn Lys Ile Leu Phe Ile
                325                 330                 335
```

-continued

Ala Gly His Asp Thr Asn Ile Ala Asn Ile Ser Gly Met Leu Gly Met
            340                 345                 350

Thr Trp Thr Leu Pro Gly Gln Pro Asp Asn Thr Pro Gly Gly Gly
        355                 360                 365

Leu Val Phe Glu Leu Trp Gln Asn Pro Asp Asn His Gln Gln Tyr Val
    370                 375                 380

Ala Val Lys Met Phe Tyr Gln Thr Met Asp Gln Leu Arg Asn Ser Glu
385                 390                 395                 400

Lys Leu Asp Leu Lys Ser His Pro Ala Gly Ile Val Pro Ile Glu Ile
                405                 410                 415

Glu Gly Cys Glu Asn Ile Gly Thr Asp Lys Leu Cys Gln Leu Asp Thr
            420                 425                 430

Phe Gln Lys Arg Val Ala Gln Val Ile Glu Pro Ala Cys His Ile
        435                 440                 445

<210> SEQ ID NO 18
<211> LENGTH: 414
<212> TYPE: PRT
<213> ORGANISM: Artificial Sequence
<220> FEATURE:
<223> OTHER INFORMATION: chimeric protein

<400> SEQUENCE: 18

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
            20                  25                  30

Asn Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Ala Asp Val Asp Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Gln Gln Ala Asp Pro Leu Phe His
        115                 120                 125

Pro Val Lys Ala Gly Ile Cys Ser Met Asp Lys Ser Gln Ala His Ala
    130                 135                 140

Ala Val Glu Lys Gln Ala Gly Thr Pro Ile Glu Thr Leu Asn Gln Arg
145                 150                 155                 160

Tyr Gln Ala Ser Leu Ala Leu Met Ser Ser Val Leu Asp Phe Pro Lys
                165                 170                 175

Ser Pro Tyr Cys Gln Gln His Asn Ile Gly Lys Leu Cys Asp Phe Ser
            180                 185                 190

Gln Ala Met Pro Ser Arg Leu Ala Ile Asn Asp Gly Asn Lys Val
        195                 200                 205

Ala Leu Glu Gly Ala Val Gly Leu Ser Ser Thr Leu Ala Glu Ile Phe
    210                 215                 220

Leu Leu Glu His Ala Gln Gly Met Pro Lys Val Ala Trp Gly Asn Ile
225                 230                 235                 240

His Thr Glu Gln Gln Trp Asp Ser Leu Leu Lys Leu His Asn Ala Gln
                245                 250                 255

Phe Asp Leu Met Ser Arg Thr Pro Tyr Ile Ala Lys His Asn Gly Thr

```
                260             265             270
Pro Leu Leu Gln Thr Ile Ala His Ala Leu Gly Ser Asn Ile Ala Ser
            275                 280                 285

Arg Pro Leu Pro Asp Ile Ser Pro Asp Asn Lys Ile Leu Phe Ile Ala
        290                 295                 300

Gly His Asp Thr Asn Ile Ala Asn Ile Ser Gly Met Leu Gly Met Thr
305                 310                 315                 320

Trp Thr Leu Pro Gly Gln Pro Asp Asn Thr Pro Gly Gly Gly Leu
                325                 330                 335

Val Phe Glu Leu Trp Gln Asn Pro Asp Asn His Gln Gln Tyr Val Ala
            340                 345                 350

Val Lys Met Phe Tyr Gln Thr Met Asp Gln Leu Arg Asn Ser Glu Lys
            355                 360                 365

Leu Asp Leu Lys Ser His Pro Ala Gly Ile Val Pro Ile Glu Ile Glu
        370                 375                 380

Gly Cys Glu Asn Ile Gly Thr Asp Lys Leu Cys Gln Leu Asp Thr Phe
385                 390                 395                 400

Gln Lys Arg Val Ala Gln Val Ile Glu Pro Ala Cys His Ile
            405                 410

<210> SEQ ID NO 19
<211> LENGTH: 1245
<212> TYPE: DNA
<213> ORGANISM: Artificial Sequence
<220> FEATURE:
<223> OTHER INFORMATION: synthetic construct

<400> SEQUENCE: 19
agtgataccg cccctgctgg gttccagttg gaaaaggttg ttatcctaag cagacatggc      60
gtacgcgcgc caaccaaaat gacacaaacg atgcgcaacg tcacacctca ccagtggcct     120
gaatggccgg taaaactcgg ctatatcacg ccccgcggtg aacatctgat tagcctgatg     180
ggcggttttt atcgagagcg ctttcagcaa caaggcttat tacctaagga taactgtcct     240
acaccagatg ccgtgtatgt ttgggcagac gtcgatcaac gcacacgtaa accggcgag     300
gccttcttag cgggtcttgc tccccagtgt gatttagcga tccaccatca gcaaacatt     360
cagcaggccg atccgctgtt ccatcctgtg aaagccggta tctgttcgat ggataaatca     420
caggcacacg ccgccgttga aaagcaggca ggcacaccga ttgagacgct caatcaacgc     480
tatcaagcat ctttagcgct gatgagttcg gtactcgatt ttccaaaatc cccctattgt     540
cagcagcaca acattggcaa actctgcgat ttttcacagg cgatgcctag caggctggcg     600
ataaatgacg acggtaataa agtggctctc gaaggtgccg tgggactttc atcgacgttg     660
gctgaaattt tcctgctgga acacgctcag ggaatgccta agtggcttg ggggaatatt     720
cacactgagc agcaatggga ctctctgtta aaattgcata atgcgcagtt tgacttgatg     780
tcgcgcacgc cctatatcgc caagcataac ggtactccac tgctgcaaac catcgcacac     840
gcactgggtt ccaatatcgc gagtcgccca ctgccggata tttcgccaga caataagatc     900
ctgtttattg ccggtcacga caccaatatt gccaatattt ctggcatgct agggatgaca     960
tggacacttc cgggacagcc cgataacacc ccgccgggtg gggggctggt gtttgaacta    1020
tggcagaatc cagataacca tcagcaatat gtcgcagtta agatgttcta tcaaacaatg    1080
gatcagttac gaaatagtga aaagttagac ctgaaaagtc atccagccgg tattgttccc    1140
attgagatcg aaggttgtga gaacatcggt acagacaaac tttgccagct tgataccttc    1200
caaaagagag tggctcaggt gattgaacct gcatgccata tttaa                    1245
```

<210> SEQ ID NO 20
<211> LENGTH: 6729
<212> TYPE: DNA
<213> ORGANISM: Artificial Sequence
<220> FEATURE:
<223> OTHER INFORMATION: synthetic construct

<400> SEQUENCE: 20

| | | | | | |
|---|---|---|---|---|---|
| agcttgcggc | cgcactcgag | caccaccacc | accaccactg | agatccggct | gctaacaaag | 60 |
| cccgaaagga | agctgagttg | gctgctgcca | ccgctgagca | ataactagca | taacccttg | 120 |
| gggcctctaa | acgggtcttg | aggggttttt | tgctgaaagg | aggaactata | tccggattgg | 180 |
| cgaatgggac | gcgccctgta | gcggcgcatt | aagcgcggcg | ggtgtggtgg | ttacgcgcag | 240 |
| cgtgaccgct | acacttgcca | gcgccctagc | gcccgctcct | ttcgctttct | tcccttcctt | 300 |
| tctcgccacg | ttcgccggct | ttccccgtca | agctctaaat | cggggctcc | ctttagggtt | 360 |
| ccgatttagt | gctttacggc | acctcgaccc | caaaaaactt | gattagggtg | atggttcacg | 420 |
| tagtgggcca | tcgccctgat | agacggtttt | tcgccctttg | acgttggagt | ccacgttctt | 480 |
| taatagtgga | ctcttgttcc | aaactggaac | aacactcaac | cctatctcgg | tctattcttt | 540 |
| tgatttataa | gggattttgc | cgatttcggc | ctattggtta | aaaaatgagc | tgatttaaca | 600 |
| aaaatttaac | gcgaatttta | acaaaatatt | aacgtttaca | atttcaggtg | gcacttttcg | 660 |
| gggaaatgtg | cgcggaaccc | ctatttgttt | attttctaa | atacattcaa | atatgtatcc | 720 |
| gctcatgaga | caataaccct | gataaatgct | tcaataatat | tgaaaaagga | agagtatgag | 780 |
| tattcaacat | ttccgtgtcg | cccttattcc | cttttttgcg | gcattttgcc | ttcctgtttt | 840 |
| tgctcaccca | gaaacgctgg | tgaaagtaaa | agatgctgaa | gatcagttgg | gtgcacgagt | 900 |
| gggttacatc | gaactggatc | tcaacagcgg | taagatcctt | gagagttttc | gccccgaaga | 960 |
| acgttttcca | atgatgagca | cttttaaagt | tctgctatgt | ggcgcggtat | tatcccgtat | 1020 |
| tgacgccggg | caagagcaac | tcggtcgccg | catacactat | tctcagaatg | acttggttga | 1080 |
| gtactcacca | gtcacagaaa | agcatcttac | ggatggcatg | acagtaagag | aattatgcag | 1140 |
| tgctgccata | accatgagtg | ataacactgc | ggccaactta | cttctgacaa | cgatcggagg | 1200 |
| accgaaggag | ctaaccgctt | ttttgcacaa | catgggggat | catgtaactc | gccttgatcg | 1260 |
| ttgggaaccg | gagctgaatg | aagccatacc | aaacgacgag | cgtgacacca | cgatgcctgc | 1320 |
| agcaatggca | acaacgttgc | gcaaactatt | aactggcgaa | ctacttactc | tagcttcccg | 1380 |
| gcaacaatta | atagactgga | tggaggcgga | taaagttgca | ggaccacttc | tgcgctcggc | 1440 |
| ccttccggct | ggctggttta | ttgctgataa | atctggagcc | ggtgagcgtg | ggtctcgcgg | 1500 |
| tatcattgca | gcactggggc | cagatggtaa | gccctcccgt | atcgtagtta | tctacacgac | 1560 |
| ggggagtcag | gcaactatgg | atgaacgaaa | tagacagatc | gctgagatag | gtgcctcact | 1620 |
| gattaagcat | tggtaactgt | cagaccaagt | ttactcatat | atactttaga | ttgatttaaa | 1680 |
| acttcatttt | taatttaaaa | ggatctaggt | gaagatcctt | tttgataatc | tcatgaccaa | 1740 |
| aatcccttaa | cgtgagtttt | cgttccactg | agcgtcagac | cccgtagaaa | agatcaaagg | 1800 |
| atcttcttga | gatcctttt | ttctgcgcgt | aatctgctgc | ttgcaaacaa | aaaaaccacc | 1860 |
| gctaccagcg | gtggtttgtt | tgccggatca | agagctacca | actctttttc | cgaaggtaac | 1920 |
| tggcttcagc | agagcgcaga | taccaaatac | tgtccttcta | gtgtagccgt | agttaggcca | 1980 |
| ccacttcaag | aactctgtag | caccgcctac | atacctcgct | ctgctaatcc | tgttaccagt | 2040 |
| ggctgctgcc | agtggcgata | agtcgtgtct | taccggggttg | gactcaagac | gatagttacc | 2100 |

```
ggataaggcg cagcggtcgg gctgaacggg gggttcgtgc acacagccca gcttggagcg   2160
aacgacctac accgaactga gatacctaca gcgtgagcta tgagaaagcg ccacgcttcc   2220
cgaagggaga aaggcggaca ggtatccggt aagcggcagg gtcggaacag gagagcgcac   2280
gagggagctt ccagggggaa acgcctggta tctttatagt cctgtcgggt ttcgccacct   2340
ctgacttgag cgtcgatttt tgtgatgctc gtcaggggg cggagcctat ggaaaaacgc    2400
cagcaacgcg gccttttac ggttcctggc cttttgctgg ccttttgctc acatgttctt    2460
tcctgcgtta tccctgatt ctgtggataa ccgtattacc gcctttgagt gagctgatac    2520
cgctcgccgc agccgaacga ccgagcgcag cgagtcagtg agcgaggaag cggaagagcg   2580
cctgatgcgg tattttctcc ttacgcatct gtgcggtatt tcacaccgca tatatggtgc    2640
actctcagta caatctgctc tgatgccgca tagttaagcc agtatacact ccgctatcgc    2700
tacgtgactg ggtcatggct gcgccccgac acccgccaac accgctgac gcgccctgac     2760 gggcttgtct gctcccggca tccgcttaca gacaagctgt gaccgtctcc gggagctgca   2820
tgtgtcagag gttttcaccg tcatcaccga aacgcgcgag gcagctgcgg taaagctcat   2880
cagcgtggtc gtgaagcgat tcacagatgt ctgcctgttc atccgcgtcc agctcgttga   2940
gtttctccag aagcgttaat gtctggcttc tgataaagcg ggccatgtta agggcggttt   3000
tttcctgttt ggtcactgat gcctccgtgt aaggggatt tctgttcatg ggggtaatga    3060
taccgatgaa acgagagagg atgctcacga tacgggttac tgatgatgaa catgcccggt    3120
tactggaacg ttgtgagggt aaacaactgg cggtatggat gcggcgggac cagagaaaaa    3180
tcactcaggg tcaatgccag cgcttcgtta atacagatgt aggtgttcca cagggtagcc    3240
agcagcatcc tgcgatgcag atccggaaca taatggtgca gggcgctgac ttccgcgttt    3300
ccagacttta cgaaacacgg aaaccgaaga ccattcatgt tgttgctcag gtcgcagacg    3360
ttttgcagca gcagtcgctt cacgttcgct cgcgtatcgg tgattcattc tgctaaccag    3420
taaggcaacc ccgccagcct agccgggtcc tcaacgacag gagcacgatc atgcgcaccc    3480
gtggggccgc catgccggcg ataatggcct gcttctcgcc gaaacgtttg gtggcgggac    3540
cagtgacgaa ggcttgagcg agggcgtgca agattccgaa taccgcaagc gacaggccga    3600
tcatcgtcgc gctccagcga aagcggtcct cgccgaaaat gacccagagc gctgccggca    3660
cctgtcctac gagttgcatg ataaagaaga cagtcataag tgcggcgacg atagtcatgc    3720
cccgcgccca ccggaaggag ctgactgggt tgaaggctct caagggcatc ggtcgagatc    3780
ccggtgccta atgagtgagc taacttacat taattgcgtt gcgctcactg cccgctttcc    3840
agtcgggaaa cctgtcgtgc cagctgcatt aatgaatcgg ccaacgcgcg gggagaggcg    3900
gtttgcgtat tgggcgccag ggtggttttt cttttcacca gtgagacggg caacagctga   3960
ttgcccttca ccgcctggcc ctgagagagt tgcagcaagc ggtccacgct ggtttgcccc    4020
agcaggcgaa aatcctgttt gatggtggtt aacggcggga tataacatga gctgtcttcg    4080
gtatcgtcgt atcccactac cgagatatcc gcaccaacgc gcagcccgga ctcggtaatg    4140
gcgcgcattg cgcccagcgc catctgatcg ttggcaacca gcatcgcagt gggaacgatg    4200
ccctcattca gcatttgcat ggtttgttga aaaccggaca tggcactcca gtcgccttcc    4260
cgttccgcta tcggctgaat ttgattgcga gtgagatatt tatgccagcc agccagacgc    4320
agacgcgccg agacagaact taatgggccc gctaacagcg cgatttgctg gtgacccaat    4380
gcgaccagat gctccacgcc cagtcgcgta ccgtcttcat gggagaaaat aatactgttg    4440
atgggtgtct ggtcagagac atcaagaaat aacgccggaa cattagtgca ggcagcttcc    4500
```

```
acagcaatgg catcctggtc atccagcgga tagttaatga tcagcccact gacgcgttgc    4560
gcgagaagat tgtgcaccgc cgctttacag gcttcgacgc cgcttcgttc taccatcgac    4620
accaccacgc tggcacccag ttgatcggcg cgagatttaa tcgccgcgac aatttgcgac    4680
ggcgcgtgca gggccagact ggaggtggca acgccaatca gcaacgactg tttgcccgcc    4740
agttgttgtg ccacgcggtt gggaatgtaa ttcagctccg ccatcgccgc ttccactttt    4800
tcccgcgttt tcgcagaaac gtggctggcc tggttcacca cgcgggaaac ggtctgataa    4860
gagacaccgg catactctgc gacatcgtat aacgttactg gtttcacatt caccaccctg    4920
aattgactct cttccgggcg ctatcatgcc ataccgcgaa aggttttgcg ccattcgatg    4980
gtgtccggga tctcgacgct ctcccttatg cgactcctgc attaggaagc agcccagtag    5040
taggttgagg ccgttgagca ccgccgccgc aaggaatggt gcatgcaagg agatggcgcc    5100
caacagtccc ccggccacgg ggcctgccac catacccacg ccgaaacaag cgctcatgag    5160
cccgaagtgg cgagcccgat cttccccatc ggtgatgtcg gcgatatagg cgccagcaac    5220
cgcacctgtg gcgccggtga tgccggccac gatgcgtccg gcgtagagga tcgagatctc    5280
gatcccgcga aattaatacg actcactata ggggaattgt gagcggataa caattcccct    5340
ctagaaataa ttttgtttaa ctttaagaag gagatataca tatgatgaca atctctctgt    5400
ttaaccgtaa taaacccgct attgcacagc gtatttatg tcctctgatc gtggctttat    5460
tctcaggttt accggcatac gccagtgata ccgcccctgc tgggttccag ttggaaaagg    5520
ttgttatcct aagcagacat ggcgtacgcg cgccaaccaa aatgacacaa acgatgcgca    5580
acgtcacacc tcaccagtgg cctgaatggc cggtaaaact cggctatatc acgccccgcg    5640
gtgaacatct gattagcctg atgggcggtt tttatcgaga cgctttcag caacaaggct    5700 tattacctaa ggataactgt cctacaccag atgccgtgta tgtttgggca gacgtcgatc    5760
aacgcacacg taaaaccggc gaggccttct tagcgggtct tgctccccag tgtgatttag    5820
cgatccacca tcagcaaaac attcagcagg ccgatccgct gttccatcct gtgaaagccg    5880
gtatctgttc gatggataaa tcacaggcac acgccgccgt tgaaaagcag gcaggcacac    5940
cgattgagac gctcaatcaa cgctatcaag catctttagc gctgatgagt tcggtactcg    6000
attttccaaa atcccctat tgtcagcagc acaacattgg caaactctgc gattttcac    6060 aggcgatgcc tagcaggctg gcgataaatg acgacggtaa taagtggct ctcgaaggtg    6120 ccgtgggact ttcatcgacg ttggctgaaa ttttcctgct ggaacacgct cagggaatgc    6180
ctaaagtggc ttgggggaat attcacactg agcagcaatg ggactctctg ttaaaattgc    6240
ataatgcgca gtttgacttg atgtcgcgca cgccctatat cgccaagcat aacggtactc    6300
cactgctgca aaccatcgca cacgcactgg gttccaatat cgcgagtcgc ccactgccgg    6360
atatttcgcc agacaataag atcctgttta ttgccggtca cgacaccaat attgccaata    6420
tttctggcat gctagggatg acatggacac ttccgggaca gcccgataac accccgccgg    6480 gtgggggggct ggtgtttgaa ctatggcaga atccagataa ccatcagcaa tatgtcgcag    6540
ttaagatgtt ctatcaaaca atggatcagt tacgaaatag tgaaaagtta gacctgaaaa    6600
gtcatccagc cggtattgtt cccattgaga tcgaaggttg tgagaacatc ggtacagaca    6660
aactttgcca gcttgatacc ttccaaaaga gagtggctca ggtgattgaa cctgcatgcc    6720
atatttaaa                                                            6729
```

<210> SEQ ID NO 21
<211> LENGTH: 46

```
<212> TYPE: DNA
<213> ORGANISM: Artificial Sequence
<220> FEATURE:
<223> OTHER INFORMATION: primer

<400> SEQUENCE: 21
ctatggatcc gcatcatcat catcatcaca gtgataccgc ccctgc                    46

<210> SEQ ID NO 22
<211> LENGTH: 6738
<212> TYPE: DNA
<213> ORGANISM: Artificial Sequence
<220> FEATURE:
<223> OTHER INFORMATION: synthetic construct

<400> SEQUENCE: 22
gagatataca tatgaaatac ctgctgccga ccgctgctgc tggtctgctg ctcctcgctg      60
cccagccggc gatggccatg gatatcggaa ttaattcgga tccgcatcat catcatcatc    120
acagtgatac cgcccctgct gggttccagt tggaaaaggt tgttatccta agcagacatg    180
gcgtacgcgc gccaaccaaa atgacacaaa cgatgcgcaa cgtcacacct caccagtggc    240
ctgaatggcc ggtaaaactc ggctatatca cgccccgcgg tgaacatctg attagcctga    300
tgggcggttt ttatcgagag cgctttcagc aacaaggctt attacctaag gataactgtc    360
ctacaccaga tgccgtgtat gtttgggcag acgtcgatca acgcacacgt aaaaccggcg    420
aggccttctt agcgggtctt gctccccagt gtgatttagc gatccaccat cagcaaaaca    480
ttcagcaggc cgatccgctg ttccatcctg tgaaagccgg tatctgttcg atggataaat    540
cacaggcaca cgccgccgtt gaaaagcagg caggcacacc gattgagacg ctcaatcaac    600
gctatcaagc tctttagcg ctgatgagtt cggtactcga ttttccaaaa tcccctatt     660 gtcagcagca caacattggc aaactctgcg atttttcaca ggcgatgcct agcaggctgg    720
cgataaatga cgacggtaat aaagtggctc tcgaaggtgc cgtgggactt tcatcgacgt    780
tggctgaaat tttcctgctg aacacgctc agggaatgcc taaagtggct tggggaata    840 ttcacactga gcagcaatgg gactctctgt taaaattgca taatgcgcag tttgacttga    900
tgtcgcgcac gccctatatc gccaagcata acggtactcc actgctgcaa accatcgcac    960
acgcactggg ttccaatatc gcgagtcgcc cactgccgga tatttcgcca gacaataaga   1020 tcctgttat tgccggtcac gacaccaata ttgccaatat ttctggcatg ctagggatga   1080
catggacact tccgggacag cccgataaca ccccgccggg tgggggctg gtgtttgaac   1140 tatggcagaa tccagataac catcagcaat atgtcgcagt aagatgttc tatcaaacaa    1200 tggatcagtt acgaaatagt gaaaagttag acctgaaaag tcatccagcc ggtattgttc    1260
ccattgagat cgaaggttgt gagaacatcg gtacagacaa actttgccag cttgatacct    1320
tccaaaagag agtggctcag gtgattgaac ctgcatgcca tatttaaaag cttgcggccg    1380
cactcgagca ccaccaccac caccactgag atccggctgc taacaaagcc cgaaaggaag    1440
ctgagttggc tgctgccacc gctgagcaat aactagcata accccttggg gcctctaaac    1500
gggtcttgag gggttttttg ctgaaaggag gaactatatc cggattggcg aatgggacgc    1560
gccctgtagc ggcgcattaa gcgcggcggg tgtggtggtt acgcgcagcg tgaccgctac    1620
acttgccagc gccctagcgc ccgctccttt cgctttcttc ccttcctttc tcgccacgtt    1680
cgccggcttt ccccgtcaag ctctaaatcg ggggctccct ttagggttcc gatttagtgc    1740
tttacggcac ctcgacccca aaaaacttga ttagggtgat ggttcacgta gtgggccatc    1800
gccctgatag acggtttttc gccctttgac gttggagtcc acgttcttta atagtggact    1860
```

```
cttgttccaa actggaacaa cactcaaccc tatctcggtc tattcttttg atttataagg    1920
gattttgccg atttcggcct attggttaaa aaatgagctg atttaacaaa aatttaacgc    1980
gaattttaac aaaatattaa cgtttacaat ttcaggtggc acttttcggg gaaatgtgcg    2040
cggaacccct atttgtttat ttttctaaat acattcaaat atgtatccgc tcatgagaca    2100
ataaccctga taaatgcttc aataatattg aaaaaggaag agtatgagta ttcaacattt    2160
ccgtgtcgcc cttattccct ttttttgcggc attttgcctt cctgttttttg ctcacccaga    2220 aacgctggtg aaagtaaaag atgctgaaga tcagttgggt gcacgagtgg gttacatcga    2280
actggatctc aacagcggta agatccttga gagttttcgc cccgaagaac gttttccaat    2340
gatgagcact tttaaagttc tgctatgtgg cgcggtatta tcccgtattg acgccgggca    2400
agagcaactc ggtcgccgca tacactattc tcagaatgac ttggttgagt actcaccagt    2460
cacagaaaag catcttacgg atggcatgac agtaagagaa ttatgcagtg ctgccataac    2520
catgagtgat aacactgcgg ccaacttact tctgacaacg atcggaggac cgaaggagct    2580
aaccgctttt ttgcacaaca tgggggatca tgtaactcgc cttgatcgtt gggaaccgga    2640
gctgaatgaa gccataccaa acgacgagcg tgacaccacg atgcctgcag caatggcaac    2700
aacgttgcgc aaactattaa ctggcgaact acttactcta gcttcccggc aacaattaat    2760
agactggatg gaggcggata agttgcagg accacttctg cgctcggccc ttccggctgg    2820
ctggtttatt gctgataaat ctggagccgg tgagcgtggg tctcgcggta tcattgcagc    2880
actggggcca gatggtaagc cctcccgtat cgtagttatc tacacgacgg ggagtcaggc    2940
aactatggat gaacgaaata gacagatcgc tgagataggt gcctcactga ttaagcattg    3000
gtaactgtca gaccaagttt actcatatat actttagatt gatttaaaac ttcattttta    3060
atttaaaagg atctaggtga agatccttt tgataatctc atgaccaaaa tcccttaacg    3120
tgagttttcg ttccactgag cgtcagaccc cgtagaaaag atcaaggat cttcttgaga    3180 tcctttttt ctgcgcgtaa tctgctgctt gcaaacaaaa aaaccaccgc taccagcggt    3240
ggtttgtttg ccggatcaag agctaccaac tcttttttccg aaggtaactg gcttcagcag    3300
agcgcagata ccaaatactg tccttctagt gtagccgtag ttaggccacc acttcaagaa    3360
ctctgtagca ccgcctacat acctcgctct gctaatcctg ttaccagtgg ctgctgccag    3420
tggcgataag tcgtgtctta ccgggttgga ctcaagacga tagttaccgg ataaggcgca    3480
gcggtcgggc tgaacggggg gttcgtgcac acagcccagc ttggagcgaa cgacctacac    3540
cgaactgaga tacctacagc gtgagctatg agaaagcgcc acgcttcccg aagggagaaa    3600
ggcggacagg tatccggtaa gcggcagggt cggaacagga gagcgcacga gggagcttcc    3660
agggggaaac gcctggtatc tttatagtcc tgtcgggttt cgccacctct gacttgagcg    3720
tcgatttttg tgatgctcgt cagggggcg gagcctatgg aaaaacgcca gcaacgcggc    3780 cttttttacgg ttcctggcct tttgctggcc ttttgctcac atgttctttc ctgcgttatc    3840
ccctgattct gtggataacc gtattaccgc ctttgagtga gctgataccg ctcgccgcag    3900
ccgaacgacc gagcgcagcg agtcagtgag cgaggaagcg gaagagcgcc tgatgcggta    3960
ttttctcctt acgcatctgt gcggtatttc acaccgcata tggtgcac tctcagtaca    4020 atctgctctg atgccgcata gttaagccag tatacactcc gctatcgcta cgtgactggg    4080
tcatggctgc gccccgacac ccgccaacac ccgctgacgc gccctgacgg gcttgtctgc    4140
tcccggcatc cgcttacaga caagctgtga ccgtctccgg gagctgcatg tgtcagaggt    4200
tttcaccgtc atcaccgaaa cgcgcgaggc agctgcggta aagctcatca gcgtggtcgt    4260
```

```
gaagcgattc acagatgtct gcctgttcat ccgcgtccag ctcgttgagt ttctccagaa   4320
gcgttaatgt ctggcttctg ataaagcggg ccatgttaag ggcggttttt tcctgtttgg   4380
tcactgatgc ctccgtgtaa gggggatttc tgttcatggg ggtaatgata ccgatgaaac   4440
gagagaggat gctcacgata cgggttactg atgatgaaca tgcccggtta ctggaacgtt   4500
gtgagggtaa acaactggcg gtatggatgc ggcgggacca gagaaaaatc actcagggtc   4560
aatgccagcg cttcgttaat acagatgtag gtgttccaca gggtagccag cagcatcctg   4620
cgatgcagat ccggaacata atggtgcagg gcgctgactt ccgcgtttcc agactttacg   4680
aaacacggaa accgaagacc attcatgttg ttgctcaggt cgcagacgtt ttgcagcagc   4740
agtcgcttca cgttcgctcg cgtatcggtg attcattctg ctaaccagta aggcaacccc   4800
gccagcctag ccgggtcctc aacgacagga gcacgatcat cgcacccgt ggggccgcca    4860 tgccggcgat aatggcctgc ttctcgccga aacgtttggt ggcgggacca gtgacgaagg   4920
cttgagcgag ggcgtgcaag attccgaata ccgcaagcga caggccgatc atcgtcgcgc   4980
tccagcgaaa gcggtcctcg ccgaaaatga cccagagcgc tgccggcacc tgtcctacga   5040
gttgcatgat aaagaagaca gtcataagtg cggcgacgat agtcatgccc cgcgcccacc   5100
ggaaggagct gactgggttg aaggctctca agggcatcgg tcgagatccc ggtgcctaat   5160
gagtgagcta acttacatta attgcgttgc gctcactgcc cgctttccag tcgggaaacc   5220
tgtcgtgcca gctgcattaa tgaatcggcc aacgcgcggg gagaggcggt ttgcgtattg   5280
ggcgccaggg tggttttct tttcaccagt gagacgggca acagctgatt gcccttcacc    5340
gcctggccct gagagagttg cagcaagcgg tccacgctgg tttgccccag caggcgaaaa   5400
tcctgtttga tggtggttaa cggcgggata taacatgagc tgtcttcggt atcgtcgtat   5460
cccactaccg agatatccgc accaacgcgc agcccggact cggtaatggc gcgcattgcg   5520
cccagcgcca tctgatcgtt ggcaaccagc atcgcagtgg gaacgatgcc ctcattcagc   5580
atttgcatgg tttgttgaaa accggacatg gcactccagt cgccttcccg ttccgctatc   5640
ggctgaattt gattgcgagt gagatattta tgccagccag ccagacgcag acgcgccgag   5700
acagaactta atgggcccgc taacagcgcg atttgctggt gacccaatgc gaccagatgc   5760
tccacgccca gtcgcgtacc gtcttcatgg gagaaaataa tactgttgat gggtgtctgg   5820
tcagagacat caagaaataa cgccggaaca ttagtgcagg cagcttccac agcaatggca   5880
tcctggtcat ccagcggata gttaatgatc agcccactga cgcgttgcgc gagaagattg   5940
tgcaccgccg ctttacaggc ttcgacgccg cttcgttcta ccatcgacac caccacgctg   6000
gcacccagtt gatcggcgcg agatttaatc gccgcgacaa tttgcgacgg cgcgtgcagg   6060
gccagactgg aggtggcaac gccaatcagc aacgactgtt tgcccgccag ttgttgtgcc   6120
acgcggttgg gaatgtaatt cagctccgcc atcgccgctt ccactttttc ccgcgttttc   6180
gcagaaacgt ggctggcctg gttcaccacg cgggaaacgg tctgataaga gacaccggca   6240
tactctgcga catcgtataa cgttactggt ttcacattca ccaccctgaa ttgactctct   6300
tccgggcgct atcatgccat accgcgaaag gttttgcgcc attcgatggt gtccgggatc   6360
tcgacgctct cccttatgcg actcctgcat taggaagcag cccagtagta ggttgaggcc   6420
gttgagcacc gccgccgcaa ggaatggtgc atgcaaggag atgcgcccca acagtccccc   6480
ggccacgggg cctgccacca tacccacgcc gaaacaagcg ctcatgagcc cgaagtggcg   6540
agcccgatct tccccatcgg tgatgtcggc gatataggcg ccagcaaccg cacctgtggc   6600
gccggtgatg ccggccacga tgcgtccggc gtagaggatc gagatctcga tcccgcgaaa   6660
```

```
ttaatacgac tcactatagg ggaattgtga gcggataaca attcccctct agaaataatt    6720
ttgtttaact ttaagaag                                                   6738

<210> SEQ ID NO 23
<211> LENGTH: 10331
<212> TYPE: DNA
<213> ORGANISM: Artificial Sequence
<220> FEATURE:
<223> OTHER INFORMATION: synthetic construct

<400> SEQUENCE: 23
aagcttgcat gagcatgtca cagtcgaatt ctggggtcac gcggtgcttg agggcgaata      60
cggctccatc ggtgagtaac ctctctctta ctaccacgga acatcactg acgtaaccag      120 gacccggcgg cttatccatc atgggaaaca acacctacaa atccgccaga attctctcgg    180
aagaatataa cctctactac tccgtctggt gcgacggtga ccacgagctg tacgatctct    240
cagtaagtgc caaccggttc ccgccactat cgtaaaaaca aaaatctaa caacaccaga    300 cggacccta ccaaatgaac aacatctaca cccaacaaga caacatccac ctcctaagca    360
gacctctatc cagcgtgatt gatcgtatcg acgctctcct tctggttctg aaatcctgca    420
agggtaacac atgcatccag ccgtggcggg tcctccaccc cgacgggtcc gtagagagcc    480
tcaaagatgc actgcaggtg aaatacgatt ccttttacac caaccagccc aaggtgtcgt    540
attcagtatg tgaacccggg tacatcattg aggctgaggg gccccaggtc ggattgcagt    600
atagagatgg gctgagttgg gaggcgtgga cttgacgatt ccgtcaagta tgagtatggg    660
tacgaataat gagcgttatt gctatgtatt tttatagata gtttatttat atatcatgac    720
taaacttgag agccatggaa tcaatgaaat gacatggcga gtgtagatca cgatagtcat    780
agtagccgaa gtgggcggat agccaagaat aacaccagaa tcagataaca ggaacatcac    840
aaccgatcac accatagata atatccaaag aagttaaaat agccgagaca agagaatag    900 agacaagata catggaacaa gaaaggtaca cccggtagat aaaccctggg acgggcccga    960
gtccttaccc atagatcaat cccacgggaa caaaaccaaa gtcaacaacc accaccacca    1020
ttaccacaac cgcatcaata gaaccggtga aaaatgacac catcgaatcc ttcaccctaa    1080
gtaaagccct gtacgttgca tatcgcttaa gcacaaaagt agtagaatag atatgagccc    1140
gcacgcgcgg ccaacgatcc aaactagccc tgacatcaaa gccagcggcg attgcgccat    1200
caagcccccg tctcacttca tagtggaatt gcgggtcacc tcactgattg actgtctgtc    1260
tagacacact cacccacgca tgctgtctgt gcccagaacg tggactttgg ctctgccgag    1320
ctagaggatc aaatataagt agattggatg taggcccgta tttttttat ttcgtgtgac    1380 tcggagattt tatgcgttgt gttgttgggc ggaaaaagaa atatactttc tttttgttct    1440
tttctttttc tctctattgc ttgccttgga tatcccttgc atacggtcgg ttgctgattg    1500
actaagggtg ctgtcttgtg tcactgaact gctgctcaac ctctgtctgg tattcctgtt    1560
gtcgtgatgg tggggaaaca gttcgagttc gaggaccaga gggatggcat cgtgcctccc    1620
ttggaggaaa agaaggtcgt cgatgaggtc tataccgata tgatgttgc gtcggaggag    1680 attgtcaagg actgggatga taaggaggag ggcaagctgc ggaggaagtg agtcgtcact    1740
gttttcattc actgccatat aggttcaagc atatactgac tggtatatag gatcgatatc    1800
atcctcatcc ccattctcgc tctcgctttc ttcggcctcc agattgatcg cggcaatatc    1860
agcgcagctc ttacctccac tatcaccgaa gacctaggtg tcaccacgaa ccaaatcaat    1920
attggaaccc agttgctttc ggctggtatt gtcatcaccg agatcccgtc aaatattata    1980
```

```
cttcagcgca tcggtcccca ggtctggttg tcggcacagc tgatcgcttg gggtctggtt    2040
ggcacattcc aggcttttgt acagtcgtac ccggcgtatc tggccacgag gttgttgctg    2100
gggctgttgg agggagggtt tattcctggt ttgtctggtc gtgcgccttg gtctatggtg    2160
gtagcgctaa caatgggttt ggtacaggtg ccctgtacta tctctcgaca tggtataaac    2220
gtcctgagac gagtttccgg accactctgt tcttctatgg gcagatgttt gccggtgcga    2280
cctcgagcgg ccgcttcgag gattgcctga acattgacat tcggcgtccg gccgggacca    2340
ccgcggactc gaagctgcct gtgctggtct ggatctttgg cggaggcttt gaacttggtt    2400
caaaggcgat gtatgatggt acaacgatgg tatcatcgtc gatagacaag aacatgccta    2460
tcgtgtttgt agcaatgaat tatcgcgtgg gaggtttcgg gttcttgccc ggaaaggaga    2520
tcctggagga cgggtccgcg aacctagggc tcctggacca acgccttgcc ctgcagtggg    2580
ttgccgacaa catcgaggcc tttggtggag acccggacaa ggtgacgatt tggggagaat    2640
cagcaggagc catttccgtt tttgatcaga tgatcttgta cgacggaaac atcacttaca    2700
aggataagcc cttgttccgg ggggccatca tggactccgg tagtgttgtt cccgcagacc    2760
ccgtcgatgg ggtcaaggga cagcaagtat atgatgcggt agtggaatct gcaggctgtt    2820
cctcttctaa cgacacccta gcttgtctgc gtgaactaga ctacaccgac ttcctcaatg    2880
cggcaaactc cgtgccaggc attttaagct accattctgt ggcgttatca tatgtgcctc    2940
gaccggacgg gacggcgttg tcggcatcac cggacgtttt gggcaaagca gggaaatatg    3000
ctcgggtccc gttcatcgtg ggcgaccaag aggatgaggg gaccttattc gccttgtttc    3060
agtccaacat tacgacgatc gacgaggtgg tcgactacct ggcctcatac ttcttctatg    3120
acgctagccg agagcagctt gaagaactag tggccctgta cccagacacc accacgtacg    3180
ggtctccgtt caggacaggc gcggccaaca actggtatcc gcaatttaag cgattggccg    3240
ccattctcgg cgacttggtc ttcaccatta cccggcgggc attcctctcg tatgcagagg    3300
aaatctcccc tgatcttccg aactggtcgt acctggcgac ctatgactat ggcaccccag    3360
ttctggggac cttccacgga agtgacctgc tgcaggtgtt ctatgggatc aagccaaact    3420
atgcagctag ttctagccac acgtactatc tgagctttgt gtatacgctg gatccgaact    3480
ccaaccgggg ggagtacatt gagtggccgc agtggaagga atcgcggcag ttgatgaatt    3540
tcggagcgaa cgacgccagt ctccttacgg atgatttccg caacgggaca tatgagttca    3600
tcctgcagaa taccgcggcg ttccacatct gatgccattg gcggagggggt ccggacggtc    3660 aggaacttag ccttatgaga tgaatgatgg acgtgtctgg cctcggaaaa ggatatatgg    3720
ggatcatgat agtactagcc atattaatga agggcatata ccacgcgttg gacctgcgtt    3780
atagcttccc gttagttata gtaccatcgt tataccagcc aatcaagtca ccacgcacga    3840
ccggggacgg cgaatcccg ggaattgaaa gaaattgcat cccaggccag tgaggccagc    3900
gattggccac ctctccaagg cacagggcca ttctgcagcg ctggtggatt catcgcaatt    3960 tccccccggcc cggcccgaca ccgctatagg ctggttctcc cacaccatcg gagattcgtc    4020
gcctaatgtc tcgtccgttc acaagctgaa gagcttgaag tggcgagatg tctctgcagg    4080
aattcaagct agatgctaag cgatattgca tggcaatatg tgttgatgca tgtgcttctt    4140
ccttcagctt cccctcgtgc agatgaggtt tggctataaa ttgaagtggt tggtcggggt    4200
tccgtgaggg gctgaagtgc ttcctcccctt ttagacgcaa ctgagagcct gagcttcatc    4260
cccagcatca ttacacctca gcaatgggcg tctctgctgt tctacttcct ttgtatctcc    4320
tgtctgggta tgctaagcac cacaatcaaa gtctaataag gaccctccct tccgagggcc    4380
```

```
cctgaagctc ggactgtgtg ggactactga tcgctgacta tctgtgcaga gtcacctccg    4440
gactggcagt ccccagtgat accgccctg ctgggttcca gttggaaaag gttgttatcc     4500
taagcagaca tggcgtacgc gcgccaacca aaatgacaca aacgatgcgc aacgtcacac    4560
ctcaccagtg gcctgaatgg ccggtaaaac tcggctatat cacgcccgc ggtgaacatc     4620 tgattagcct gatgggcggt ttttatcgag agcgctttca gcaacaaggc ttattaccta    4680
aggataactg tcctacacca gatgccgtgt atgtttgggc agacgtcgat caacgcacac    4740
gtaaaaccgg cgaggccttc ttagcgggtc ttgctcccca gtgtgattta gcgatccacc    4800
atcagcaaaa cattcagcag gccgatccgc tgttccatcc tgtgaaagcc ggtatctgtt    4860
cgatggataa atcacaggca cacgccgccg ttgaaaagca ggcaggcaca ccgattgaga    4920
cgctcaatca acgctatcaa gcatctttag cgctgatgag ttcggtactc gattttccaa    4980
aatcccccta ttgtcagcag cacaacattg gcaaactctg cgattttca caggcgatgc     5040 ctagcaggct ggcgataaat gacgacggta ataaagtggc tctcgaaggt gccgtgggac    5100
tttcatcgac gttggctgaa attttcctgc tggaacacgc tcagggaatg cctaaagtgg    5160 cttggggaa tattcacact gagcagcaat gggactctct gttaaaattg cataatgcgc     5220
agtttgactt gatgtcgcgc acgccctata tcgccaagca taacggtact ccactgctgc    5280
aaaccatcgc acacgcactg ggttccaata tcgcagtcg cccactgccg gatatttcgc     5340
cagacaataa gatcctgttt attgccggtc acgacaccaa tattgccaat atttctggca    5400
tgctagggat gacatggaca cttccgggac agcccgataa caccccgccg ggtgggggc     5460 tggtgtttga actatggcag aatccagata accatcagca atatgtcgca gttaagatgt    5520
tctatcaaac aatggatcag ttacgaaata gtgaaaagtt agacctgaaa agtcatccag    5580
ccggtattgt tcccattgag atcgaaggtt gtgagaacat cggtacagac aaactttgcc    5640
agcttgatac cttccaaaag agagtggctc aggtgattga acctgcatgc catatttaga    5700
caatcaatcc attcgctat agttaaagga tggggatgag ggcaattggt tatatgatca     5760
tgtatgtagt gggtgtgcat aatagtagtg aaatggaagc caagtcatgt gattgtaatc    5820
gaccgacgga attgaggata tccggaaata cagacaccgt gaaagccatg gtctttcctt    5880
cgtgtagaag accagacaga cagtccctga tttaccctgc acaaagcact agaaaattag    5940
cattccatcc ttctctgctt gctctgctga tatcactgtc attcaatgca tagccatgag    6000
ctcatcttag atccaagcac gtaattccat agccgaggtc cacagtggag cagcaacatt    6060
ccccatcatt gctttcccca ggggcctccc aacgactaaa tcaagagtat atctctaccg    6120
tccaatagat cgtcttcgct tcaaaatctt tgacaattcc aagagggtcc ccatccatca    6180
aacccagttc aataatagcc gagatgcatg gtggagtcaa ttaggcagta ttgctggaat    6240
gtcggggcca gttccgggtg gtcattggcc gcctgtgatg ccatctgcca ctaaatccga    6300
tcattgatcc accgcccacg agggcgtctt tgcttttgc gcggcgtcca ggttcaactc     6360
tctctgcagc tccagtccaa cgctgactga ctagtttacc tactggtctg atcggctcca    6420
tcagagctat ggcgttatcc cgtgccgttg ctgcgcaatc gctatcttga tcgcaacctt    6480
gaactcactc ttgttttaat agtgatcttg tgacggagt gtcggtgagt gacaaccaac     6540
atcgtgcaag ggagattgat acggaattgt cgctcccatc atgatgttct tgccggcttt    6600
gttggcccta ttcgtgggat cgatgccctc ctgtgcagca gcaggtactg ctggatgagg    6660
agccatcggt ctctgcacgc aaacccaact tcctcttcat tctcacggat gatcaggatc    6720
tccggatgaa ttctccggcg tatatgccgt atacgcaggc gagaatcaag gaaaagggta    6780
```

```
ccgagttctt gaaccatttc gtcactaccg cgctttgctg tccgtcgcgc gtgagtcttt    6840
ggacgggaag acaggctcat aatactaatg tgacggatgt gaacccgcct tatggtatgg    6900
acactgcttc gatcggtctt gattcttcag cgtggttaca attgctaatg cggcataggc    6960
ggatacccca aattcgtcgc tcaaggcttc aacgaaaact tcctcccgt ttggctgcag     7020 tccgccggtt acaataccta ctacacgggg aagctgttca actcgcacag tgtcgctacc    7080
tataacgcgc cctttgtgaa cggtttcaat ggctccgact tcctcctcga cccccacaca    7140
tattcctact ggaatgcgac ataccagcga aaccatgagc ctccgcggag ttacgaggga    7200
caatatacta cggatgtgat gaaggagaag gcatcgggat tgttggcaga tgcgctggac    7260
agtgacgcgc cattcttcct gacggtcgcg ccgatcgcac cgcacacgaa catcgatgtg    7320
gaggggctga gcggtgcggg tggaccgaag atgacagagc cgctgcctgc accgagacat    7380
gcgcatttgt ttgctgatgc aaaggtgccg cggacgccta atttcaatcc ggacaaggtg    7440
tgtgatatcc tgacacagtg gtgggacgg gcactgacaa gagtaggatt ctggtgcggg     7500
gtggatccaa accatggaac tacagaacca gaccgtcatc gactacgaag accatcttta    7560
tcgccagcgt ctgcgcactt tgcaagccgt cgatgagatg gtggatgcgc tgatcacgca    7620
gctggaagaa agtgggcaga tcgacaatac ctacatcatt tacagtgctg ataacggcta    7680
ccacattggc catcaccgtc tacccccggg caagacaact ggctatgaag aggacattcg    7740
cgtaccattc tacattgcg gacctggcat tcctgaggga aagagcgttg accgtgtaac      7800
cacgcacatt gacattgcac ctacactgtt cgagttggct ggggttccct tgcgagagga    7860
ctttgacggg actccgatgc ccgtgtcgac tagcaagaag acccagtcaa gcttgcatgc    7920
ctgcaggtcg actctagagg atctgccggt ctccctatag tgagtcgtat taatttcgat    7980
aagccaggtt aacctgcatt aatgaatcgg ccaacgcgcg gggagaggcg gtttgcgtat    8040
tgggcgctct tccgcttcct cgctcactga ctcgctgcgc tcggtcgttc ggctgcggcg    8100
agcggtatca gctcactcaa aggcggtaat acggttatcc acagaatcag gggataacgc    8160
aggaaagaac atgtgagcaa aaggccagca aaaggccagg aaccgtaaaa aggccgcgtt    8220
gctggcgttt ttccataggc tccgcccccc tgacgagcat cacaaaaatc gacgctcaag    8280
tcagaggtgg cgaaacccga caggactata aagataccag gcgtttcccc ctggaagctc    8340
cctcgtgcgc tctcctgttc cgaccctgcc gcttaccgga tacctgtccg cctttctccc    8400
ttcgggaagc gtggcgcttt ctcatagctc acgctgtagg tatctcagtt cggtgtaggt    8460
cgttcgctcc aagctgggct gtgtgcacga acccccgtt cagcccgacc gctgcgcctt     8520
atccggtaac tatcgtcttg agtccaaccc ggtaagacac gacttatcgc cactggcagc    8580
agccactggt aacaggatta gcagagcgag gtatgtaggc ggtgctacag agttcttgaa    8640
gtggtggcct aactacggct acactagaag gacagtattt ggtatctgcg ctctgctgaa    8700
gccagttacc ttcggaaaaa gagttggtag ctcttgatcc ggcaaacaaa ccaccgctgg    8760
tagcggtggt ttttttgttt gcaagcagca gattacgcgc agaaaaaaag gatctcaaga    8820
agatcctttg atcttttcta cggggtctga cgctcagtgg aacgaaaact cacgttaagg    8880
gattttggtc atgagattat caaaaaggat cttcacctag atccttttaa attaaaaatg    8940
aagttttaaa tcaatctaaa gtatatatga gtaaacttgg tctgacagtt accaatgctt    9000
aatcagtgag gcacctatct cagcgatctg tctatttcgt tcatccatag ttgcctgact    9060 cccccgtcgtg tagataacta cgatacggga gggcttacca tctggcccca gtgctgcaat    9120
gataccgcga gacccacgct caccggctcc agatttatca gcaataaacc agccagccgg    9180
```

```
aagggccgag cgcagaagtg gtcctgcaac tttatccgcc tccatccagt ctattaattg  9240
ttgccgggaa gctagagtaa gtagttcgcc agttaatagt ttgcgcaacg ttgttgccat  9300
tgctacaggc atcgtggtgt cacgctcgtc gtttggtatg gcttcattca gctccggttc  9360
ccaacgatca aggcgagtta catgatcccc catgttgtgc aaaaaagcgg ttagctcctt  9420
cggtcctccg atcgttgtca gaagtaagtt ggccgcagtg ttatcactca tggttatggc  9480
agcactgcat aattctctta ctgtcatgcc atccgtaaga tgcttttctg tgactggtga  9540
gtactcaacc aagtcattct gagaatagtg tatgcggcga ccgagttgct cttgcccggc  9600
gtcaatacgg gataataccg cgccacatag cagaacttta aaagtgctca tcattggaaa  9660
acgttcttcg gggcgaaaac tctcaaggat cttaccgctg ttgagatcca gttcgatgta  9720
acccactcgt gcacccaact gatcttcagc atctttttact ttcaccagcg tttctgggtg  9780
agcaaaaaca ggaaggcaaa atgccgcaaa aagggaata agggcgacac ggaaatgttg  9840
aatactcata ctcttccttt ttcaatatta ttgaagcatt tatcagggtt attgtctcat  9900
gagcggatac atatttgaat gtatttagaa aaataaacaa ataggggttc gcgcacatt  9960 tccccgaaaa gtgccacctg acgtctaaga accattatt atcatgacat taacctataa  10020
aaataggcgt atcacgaggc cctttcgtct cgcgcgtttc ggtgatgacg gtgaaaacct  10080
ctgacacatg cagctcccgg agacggtcac agcttgtctg taagcggatg ccgggagcag  10140
acaagcccgt cagggcgcgt cagcgggtgt tggcgggtgt cggggctggc ttaactatgc  10200
ggcatcagag cagattgtac tgagagtgca ccatatggac atattgtcgt tagaacgcgg  10260
ctacaattaa tacataacct tatgtatcat acacatacga tttaggtgac actatagaac  10320
tcgagcagct g                                                       10331
```

<210> SEQ ID NO 24
<211> LENGTH: 414
<212> TYPE: PRT
<213> ORGANISM: Artificial Sequence
<220> FEATURE:
<223> OTHER INFORMATION: synthetic construct

<400> SEQUENCE: 24

Ser Asp Thr Ala Pro Ala Gly Phe Gln Leu Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro His Gln Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Glu Arg Phe Gln Gln Gln Gly Leu Leu Pro Lys Asp Asn Cys Pro
65                  70                  75                  80

Thr Pro Asp Ala Val Tyr Val Trp Thr Asp Val Asn Gln Arg Thr Arg
                85                  90                  95

Lys Thr Gly Glu Ala Phe Leu Ala Gly Leu Ala Pro Gln Cys Asp Leu
            100                 105                 110

Ala Ile His His Gln Gln Asn Ile Thr Gln Val Asp Pro Leu Phe His
        115                 120                 125

Pro Val Lys Ala Gly Ile Cys Ser Met Asn Lys Ser Gln Thr Tyr Glu
    130                 135                 140

Ala Val Glu Lys Gln Ala Gly Gly Pro Ile Glu Thr Leu Asn Gln Arg
145                 150                 155                 160

Tyr Gln Ala Glu Leu Ala Leu Met Ser Ser Val Leu Asp Phe Pro Lys
            165                 170                 175

Ser Pro Tyr Cys Gln Gln His Asn Ile Gly Lys Leu Cys Asp Phe Ser
            180                 185                 190

Gln Ala Met Pro Ser Arg Leu Asn Ile Ser Asp Gly Asn Glu Val
            195                 200             205

Gln Leu Glu Gly Ala Val Gly Leu Gly Ser Thr Leu Ala Glu Ile Phe
    210                 215                 220

Leu Leu Glu Tyr Ala Gln Gly Met Pro Val Val Ala Trp Gly Asn Ile
225                 230                 235                 240

His Asn Glu Ser Gln Trp Lys Ser Leu Leu Asn Leu His Asn Ala His
                245                 250                 255

Phe Asn Leu Met His Arg Thr Pro Tyr Ile Ala Lys His Gln Gly Thr
            260                 265                 270

Pro Leu Leu Gln Ala Ile Ser Asn Ala Leu Asn Pro Asn Ala Thr Glu
        275                 280                 285

Ser Lys Leu Pro Asp Ile Ser Pro Asp Asn Lys Ile Leu Phe Ile Ala
    290                 295                 300

Gly His Asp Thr Asn Ile Ala Asn Ile Gly Gly Met Leu Gly Met Asn
305                 310                 315                 320

Trp Thr Leu Pro Gly Gln Pro Asp Asn Thr Pro Pro Gly Gly Leu
                325                 330                 335

Val Phe Glu Leu Trp Gln Asn Pro Asp Asn His Gln Gln Tyr Val Ala
            340                 345                 350

Val Lys Met Ile Tyr Gln Thr Met Asp Gln Leu Arg Asn Ser Glu Lys
        355                 360                 365

Leu Asp Leu Lys Ser Asn Pro Ala Gly Ile Val Pro Ile Glu Ile Glu
    370                 375                 380

Gly Cys Glu Asn Ile Gly Thr Asp Lys Leu Cys Gln Leu Asp Thr Phe
385                 390                 395                 400

Gln Lys Arg Val Ala Gln Val Ile Glu Pro Ala Cys Gln Ile
            405                 410

<210> SEQ ID NO 25
<211> LENGTH: 1245
<212> TYPE: DNA
<213> ORGANISM: Artificial Sequence
<220> FEATURE:
<223> OTHER INFORMATION: synthetic gene adapted to Aspergillus niger
      codon usage

<400> SEQUENCE: 25
agcgataccg cccccgcggg cttccagctg gagaaggtgg tcattctctc gcgtcacggt      60
gtccgagccc ccaccaagat gacacagacg atgcgcgatg tcactccaca tcagtggcct     120
gagtggcccg tgaagctcgg ctacatcact cctcgtggag aacacctcat cagcctgatg     180
ggcggtttct atagggaacg gttccagcag cagggattgc ttcccaagga caactgtccg     240
acccccgacg ccgtctacgt gtggaccgac gttaaccagc gtacccgcaa gactggagag     300
gctttcctcg ccggtcttgc gcctcagtgt gatctggcca tccaccacca gcagaacatc     360
acgcaggtcg acccgctgtt tcacccggtc aaggccggta tctgttcgat gaacaagtct     420
cagacctatg aggctgtcga gaagcaggct ggcggcccta ttgagacgct aaaccagcgc     480
taccaggccg aactggcatt gatgtcctct gtgttggatt ccccaagtc cccatattgc     540 cagcagcata acatcggcaa actgtgcgac ttttcacagg ctatgcctag ccgcctcaac     600

| | |
|---|---|
| atctccgatg acgggaatga ggtgcaactc gaaggcgccg tcggtcttgg ttccacgctc | 660 |
| gccgagatct tcctactgga atacgctcag ggtatgcctg tggtcgcctg gggcaacatt | 720 |
| cacaacgaga gccagtggaa gagcctcctt aacttgcaca cgcccatttt caacctgatg | 780 |
| cacagaacgc cctacattgc caagcaccag ggaaccccctt tacttcaggc tatcagcaac | 840 |
| gctctcaacc caaatgcaac tgagtcgaag ctccccgata tctctcccga caacaagatc | 900 |
| cttttcattg ccggccacga caccaacatc gcaaacatcg gaggcatgtt gggtatgaac | 960 |
| tggactctcc cgggccagcc agacaatact ccgcccggcg gtggactggt tttcgaactc | 1020 |
| tggcagaacc cggataacca tcagcagtac gttgcggtga agatgatcta ccagaccatg | 1080 |
| gaccagctgc gcaattccga gaagctggac ttgaagagca accctgctgg gatcgtcccc | 1140 |
| attgagatcg aaggttgcga gaacatcggt accgacaagc tgtgccagct ggatactttt | 1200 |
| cagaagcgtg ttgcccaggt cattgagccc gcgtgccaaa tctaa | 1245 |

<210> SEQ ID NO 26
<211> LENGTH: 10331
<212> TYPE: DNA
<213> ORGANISM: Artificial Sequence
<220> FEATURE:
<223> OTHER INFORMATION: synthetic construct

<400> SEQUENCE: 26

| | |
|---|---|
| aagcttgcat gagcatgtca cagtcgaatt ctggggtcac gcggtgcttg agggcgaata | 60 |
| cggctccatc ggtgagtaac ctctctctta ctaccacgga acatcactg acgtaaccag | 120 |
| gacccggcgg cttatccatc atgggaaaca acacctacaa atccgccaga attctctcgg | 180 |
| aagaatataa cctctactac tccgtctggt gcgacggtga ccacgagctg tacgatctct | 240 |
| cagtaagtgc caaccggttc ccgccactat cgtaaaaaca aaaatctaa caacaccaga | 300 |
| cggacccccta ccaaatgaac aacatctaca cccaacaaga caacatccac ctcctaagca | 360 |
| gacctctatc cagcgtgatt gatcgtatcg acgctctcct tctggttctg aaatcctgca | 420 |
| agggtaacac atgcatccag ccgtggcggg tcctccaccc cgacgggtcc gtagagagcc | 480 |
| tcaaagatgc actgcaggtg aaatacgatt cctttacac caaccagccc aaggtgtcgt | 540 |
| attcagtatg tgaacccggg tacatcattg aggctgaggg gccccaggtc ggattgcagt | 600 |
| atagagatgg gctgagttgg gaggcgtgga cttgacgatt ccgtcaagta tgagtatggg | 660 |
| tacgaataat gagcgttatt gctatgtatt tttatagata gtttatttat atatcatgac | 720 |
| taaacttgag agccatggaa tcaatgaaat gacatgcga gtgtagatca cgatagtcat | 780 |
| agtagccgaa gtgggcggat agccaagaat aacaccagaa tcagataaca ggaacatcac | 840 |
| aaccgatcac accatagata atatccaaag aagtttaaat agccgagaca agagaaatag | 900 |
| agacaagata catggaacaa gaaaggtaca cccggtagat aaaccctggg acgggcccga | 960 |
| gtccttaccc atagatcaat cccacgggaa caaaaccaaa gtcaacaacc accaccacca | 1020 |
| ttaccacaac cgcatcaata gaaccggtga aaaatgacac catcgaatcc ttcaccctaa | 1080 |
| gtaaagcccct gtacgttgca tatcgcttaa gcacaaaagt agtagaatag atatgagccc | 1140 |
| gcacgcgcgg ccaacgatcc aaactagccc tgacatcaaa gccagcggcg attgcgccat | 1200 |
| caagcccccg tctcacttca tagtggaatt gcggtcacc tcactgattg actgtctgtc | 1260 |
| tagacacact cacccacgca tgctgtctgt gcccagaacg tggactttgg ctctgccgag | 1320 |
| ctagaggatc aaatataagt agattggatg taggcccgta ttttttttat ttcgtgtgac | 1380 |
| tcggagattt tatgcgttgt gttgttgggc ggaaaaagaa atatactttc ttttttgttct | 1440 |

```
tttcttttc   tctctattgc  ttgccttgga  tatcccttgc  atacggtcgg  ttgctgattg  1500
actaagggtg  ctgtcttgtg  tcactgaact  gctgctcaac  ctctgtctgg  tattcctgtt  1560
gtcgtgatgg  tggggaaaca  gttcgagttc  gaggaccaga  gggatggcat  cgtgcctccc  1620
ttggaggaaa  agaaggtcgt  cgatgaggtc  tataccgata  atgatgttgc  gtcggaggag  1680
attgtcaagg  actgggatga  taaggaggag  ggcaagctgc  ggaggaagtg  agtcgtcact  1740
gttttcattc  actgccatat  aggttcaagc  atatactgac  tggtatatag  gatcgatatc  1800
atcctcatcc  ccattctcgc  tctcgctttc  ttcggcctcc  agattgatcg  cggcaatatc  1860
agcgcagctc  ttacctccac  tatcaccgaa  gacctaggtg  tcaccacgaa  ccaaatcaat  1920
attggaaccc  agttgctttc  ggctggtatt  gtcatcaccg  agatcccgtc  aaatattata  1980
cttcagcgca  tcggtcccca  ggtctggttg  tcggcacagc  tgatcgcttg  ggtctggtt   2040
ggcacattcc  aggcttttgt  acagtcgtac  ccggcgtatc  tggccacgag  gttgttgctg  2100
gggctgttgg  agggagggtt  tattcctggt  ttgtctggtc  gtgcgccttg  gtctatggtg  2160
gtagcgctaa  caatgggttt  ggtacaggtg  ccctgtacta  tctctcgaca  tggtataaac  2220
gtcctgagac  gagtttccgg  accactctgt  tcttctatgg  gcagatgttt  gccggtgcga  2280
cctcgagcgg  ccgcttcgag  gattgcctga  acattgacat  tcggcgtccg  gccgggacca  2340
ccgcggactc  gaagctgcct  gtgctggtct  ggatctttgg  cggaggcttt  gaacttggtt  2400
caaaggcgat  gtatgatggt  acaacgatgg  tatcatcgtc  gatagacaag  aacatgccta  2460
tcgtgtttgt  agcaatgaat  tatcgcgtgg  gaggtttcgg  gttcttgccc  ggaaaggaga  2520
tcctggagga  cgggtccgcg  aacctagggc  tcctggacca  acgccttgcc  ctgcagtggg  2580
ttgccgacaa  catcgaggcc  tttggtggag  acccggacaa  ggtgacgatt  tggggagaat  2640
cagcaggagc  catttccgtt  tttgatcaga  tgatcttgta  cgacggaaac  atcacttaca  2700
aggataagcc  cttgttccgg  ggggccatca  tggactccgg  tagtgttgtt  cccgcagacc  2760
ccgtcgatgg  ggtcaaggga  cagcaagtat  atgatgcggt  agtggaatct  gcaggctgtt  2820
cctcttctaa  cgacacccta  gcttgtctgc  gtgaactaga  ctacaccgac  ttcctcaatg  2880
cggcaaactc  cgtgccaggc  atttttaagct accattctgt  ggcgttatca  tatgtgcctc  2940
gaccggacgg  gacggcgttg  tcggcatcac  cggacgtttt  gggcaaagca  gggaaatatg  3000
ctcgggtccc  gttcatcgtg  ggcgaccaag  aggatgaggg  gaccttattc  gccttgtttc  3060
agtccaacat  tacgacgatc  gacgaggtgg  tcgactacct  ggcctcatac  ttcttctatg  3120
acgctagccg  agagcagctt  gaagaactag  tggccctgta  cccagacacc  accacgtacg  3180
ggtctccgtt  caggacaggc  gcggccaaca  actggtatcc  gcaatttaag  cgattggccg  3240
ccattctcgg  cgacttggtc  ttcaccatta  cccggcgggc  attcctctcg  tatgcagagg  3300
aaatctcccc  tgatcttccg  aactggtcgt  acctggcgac  ctatgactat  ggcacccccag 3360
ttctggggac  cttccacgga  agtgacctgc  tgcaggtgtt  ctatgggatc  aagccaaact  3420
atgcagctag  ttctagccac  acgtactatc  tgagctttgt  gtatacgctg  gatccgaact  3480
ccaaccgggg  ggagtacatt  gagtggccgc  agtggaagga  atcgcggcag  ttgatgaatt  3540
tcggagcgaa  cgacgccagt  ctccttacgg  atgatttccg  caacgggaca  tatgagttca  3600
tcctgcagaa  taccgcggcg  ttccacatct  gatgccattg  gcgagggggt  ccggacggtc  3660
aggaacttag  ccttatgaga  tgaatgatgg  acgtgtctgg  cctcggaaaa  ggatatatgg  3720
ggatcatgat  agtactagcc  atattaatga  agggcatata  ccacgcgttg  gacctgcgtt  3780
atagcttccc  gttagttata  gtaccatcgt  tataccagcc  aatcaagtca  ccacgcacga  3840
```

```
ccggggacgg cgaatccccg ggaattgaaa gaaattgcat cccaggccag tgaggccagc   3900
gattggccac ctctccaagg cacagggcca ttctgcagcg ctggtggatt catcgcaatt   3960
tcccccggcc cggcccgaca ccgctatagg ctggttctcc cacaccatcg agattcgtc    4020
gcctaatgtc tcgtccgttc acaagctgaa gagcttgaag tggcgagatg tctctgcagg   4080
aattcaagct agatgctaag cgatattgca tggcaatatg tgttgatgca tgtgcttctt   4140
ccttcagctt cccctcgtgc agatgaggtt tggctataaa ttgaagtggt tggtcggggt   4200
tccgtgaggg gctgaagtgc ttcctccctt ttagacgcaa ctgagagcct gagcttcatc   4260
cccagcatca ttacacctca gcaatgggcg tctctgctgt tctacttcct ttgtatctcc   4320
tgtctgggta tgctaagcac cacaatcaaa gtctaataag accctccct tccgagggcc    4380
cctgaagctc ggactgtgtg ggactactga tcgctgacta tctgtgcaga gtcacctccg   4440
gactggcagt ccccagcgat accgcccccg cgggcttcca gctggagaag gtggtcattc   4500
tctcgcgtca cggtgtccga gcccccacca agatgacaca gacgatgcgc gatgtcactc   4560
cacatcagtg gcctgagtgg cccgtgaagc tcggctacat cactcctcgt ggagaacacc   4620
tcatcagcct gatgggcggt ttctataggg aacggttcca gcagcaggga ttgcttccca   4680
aggacaactg tccgaccccc gacgccgtct acgtgtggac cgacgttaac cagcgtaccc   4740
gcaagactgg agaggctttc ctcgccggtc ttgcgcctca gtgtgatctg gccatccacc   4800
accagcagaa catcacgcag gtcgacccgc tgtttcaccc ggtcaaggcc ggtatctgtt   4860
cgatgaacaa gtctcagacc tatgaggctg tcgagaagca ggctggcggc cctattgaga   4920
cgctaaacca gcgctaccag gccgaactgg cattgatgtc ctctgtgttg gatttcccca   4980
agtccccata ttgccagcag cataacatcg gcaaactgtg cgacttttca caggctatgc   5040
ctagccgcct caacatctcc gatgacggga atgaggtgca actcgaaggc gccgtcggtc   5100
ttggttccac gctcgccgag atcttcctac tggaatacgc tcagggtatg cctgtggtcg   5160
cctggggcaa cattcacaac gagagccagt ggaagagcct ccttaacttg cacaacgccc   5220
atttcaacct gatgcacaga acgccctaca ttgccaagca ccagggaacc cctttacttc   5280
aggctatcag caacgctctc aacccaaatg caactgagtc gaagctcccc gatatctctc   5340
ccgacaacaa gatccttttc attgccggcc acgacaccaa catcgcaaac atcggaggca   5400
tgttgggtat gaactggact ctcccgggcc agccagacaa tactccgccc ggcggtggac   5460
tggttttcga actctggcag aacccggata accatcagca gtacgttgcg gtgaagatga   5520
tctaccagac catggaccag ctgcgcaatt ccgagaagct ggacttgaag agcaaccctg   5580
ctgggatcgt ccccattgag atcgaaggtt gcgagaacat cggtaccgac aagctgtgcc   5640
agctggatac ttttcagaag cgtgttgccc aggtcattga gcccgcgtgc caaatctaaa   5700
caatcaatcc atttcgctat agttaaagga tggggatgag ggcaattggt tatatgatca   5760
tgtatgtagt gggtgtgcat aatagtagtg aaatggaagc caagtcatgt gattgtaatc   5820
gaccgacgga attgaggata tccggaaata cagacaccgt gaaagccatg gtctttcctt   5880
cgtgtagaag accagacaga cagtccctga tttaccctgc acaaagcact agaaaattag   5940
cattccatcc ttctctgctt gctctgctga tatcactgtc attcaatgca tagccatgag   6000
ctcatcttag atccaagcac gtaattccat agccgaggtc cacagtggag cagcaacatt   6060
ccccatcatt gctttcccca ggggcctccc aacgactaaa tcaagagtat atctctaccg   6120
tccaatagat cgtcttcgct tcaaaatctt tgacaattcc aagagggtcc ccatccatca   6180
aacccagttc aataatagcc gagatgcatg gtggagtcaa ttaggcagta ttgctggaat   6240
```

```
gtcggggcca gttccgggtg gtcattggcc gcctgtgatg ccatctgcca ctaaatccga   6300
tcattgatcc accgcccacg agggcgtctt tgcttttttgc gcggcgtcca ggttcaactc   6360
tctctgcagc tccagtccaa cgctgactga ctagtttacc tactggtctg atcggctcca   6420
tcagagctat ggcgttatcc cgtgccgttg ctgcgcaatc gctatcttga tcgcaacctt   6480
gaactcactc ttgttttaat agtgatcttg gtgacggagt gtcggtgagt gacaaccaac   6540
atcgtgcaag ggagattgat acggaattgt cgctcccatc atgatgttct tgccggcttt   6600
gttggcccta ttcgtgggat cgatgccctc ctgtgcagca gcaggtactg ctggatgagg   6660
agccatcggt ctctgcacgc aaacccaact tcctcttcat tctcacggat gatcaggatc   6720
tccggatgaa ttctccggcg tatatgccgt atacgcaggc gagaatcaag gaaaagggta   6780
ccgagttctt gaaccatttc gtcactaccg cgctttgctg tccgtcgcgc gtgagtcttt   6840
ggacgggaag acaggctcat aatactaatg tgacggatgt gaacccgcct tatggtatgg   6900
acactgcttc gatcggtctt gattcttcag cgtggttaca attgctaatg cggcataggc   6960
ggatacccca aattcgtcgc tcaaggcttc aacgaaaact tcctcccgt ttggctgcag   7020 tccgccggtt acaataccta ctacacgggg aagctgttca actcgcacag tgtcgctacc   7080
tataacgcgc cctttgtgaa cggtttcaat ggctccgact tcctcctcga cccccacaca   7140
tattcctact ggaatgcgac ataccagcga aaccatgagc ctccgcggag ttacgaggga   7200
caatatacta cggatgtgat gaaggagaag gcatcgggat tgttggcaga tgcgctggac   7260
agtgacgcgc cattcttcct gacggtcgcg ccgatcgcac cgcacacgaa catcgatgtg   7320 gagggggctga gcggtgcggg tggaccgaag atgacagagc cgctgcctgc accgagacat   7380
gcgcatttgt ttgctgatgc aaaggtgccg cggacgccta atttcaatcc ggacaaggtg   7440
tgtgatatcc tgacacagtg gtggggacgg gcactgacaa gagtaggatt ctggtgcggg   7500
gtggatccaa accatggaac tacagaacca gaccgtcatc gactacgaag accatcttta   7560
tcgccagcgt ctgcgcactt tgcaagccgt cgatgagatg gtggatgcgc tgatcacgca   7620
gctggaagaa agtgggcaga tcgacaatac ctacatcatt tacagtgctg ataacggcta   7680
ccacattggc catcaccgtc tacccccccgg caagacaact ggctatgaag aggacattcg   7740
cgtaccattc tacattcgcg gacctggcat tcctgaggga agagcgttg accgtgtaac   7800 cacgcacatt gacattgcac ctacactgtt cgagttggct ggggttccct tgcgagagga   7860
ctttgacggg actccgatgc ccgtgtcgac tagcaagaag acccagtcaa gcttgcatgc   7920
ctgcaggtcg actctagagg atctgccggt ctccctatag tgagtcgtat taatttcgat   7980
aagccaggtt aacctgcatt aatgaatcgg ccaacgcgcg gggagaggcg gtttgcgtat   8040
tgggcgctct tccgcttcct cgctcactga ctcgctgcgc tcggtcgttc ggctgcggcg   8100
agcggtatca gctcactcaa aggcggtaat acggttatcc acagaatcag gggataacgc   8160
aggaaagaac atgtgagcaa aaggccagca aaaggccagg aaccgtaaaa aggccgcgtt   8220
gctggcgttt ttccataggc tccgcccccc tgacgagcat cacaaaaatc gacgctcaag   8280
tcagaggtgg cgaaacccga caggactata aagataccag gcgtttcccc ctggaagctc   8340
cctcgtgcgc tctcctgttc cgaccctgcc gcttaccgga tacctgtccg cctttctccc   8400
ttcgggaagc gtggcgcttt ctcatagctc acgctgtagg tatctcagtt cggtgtaggt   8460
cgttcgctcc aagctgggct gtgtgcacga acccccgtt cagcccgacc gctgcgcctt   8520
atccggtaac tatcgtcttg agtccaaccc ggtaagacac gacttatcgc cactggcagc   8580
agccactggt aacaggatta gcagagcgag gtatgtaggc ggtgctacag agttcttgaa   8640
```

-continued

```
gtggtggcct aactacggct acactagaag gacagtattt ggtatctgcg ctctgctgaa    8700
gccagttacc ttcggaaaaa gagttggtag ctcttgatcc ggcaaacaaa ccaccgctgg    8760
tagcggtggt ttttttgttt gcaagcagca gattacgcgc agaaaaaaag gatctcaaga    8820
agatcctttg atcttttcta cggggtctga cgctcagtgg aacgaaaact cacgttaagg    8880
gattttggtc atgagattat caaaaaggat cttcacctag atccttttaa attaaaaatg    8940
aagttttaaa tcaatctaaa gtatatatga gtaaacttgg tctgacagtt accaatgctt    9000
aatcagtgag gcacctatct cagcgatctg tctatttcgt tcatccatag ttgcctgact    9060
ccccgtcgtg tagataacta cgatacggga gggcttacca tctggcccca gtgctgcaat    9120
gataccgcga gacccacgct caccggctcc agatttatca gcaataaacc agccagccgg    9180
aagggccgag cgcagaagtg gtcctgcaac tttatccgcc tccatccagt ctattaattg    9240
ttgccgggaa gctagagtaa gtagttcgcc agttaatagt ttgcgcaacg ttgttgccat    9300
tgctacaggc atcgtggtgt cacgctcgtc gtttggtatg gcttcattca gctccggttc    9360
ccaacgatca aggcgagtta catgatcccc catgttgtgc aaaaaagcgg ttagctcctt    9420
cggtcctccg atcgttgtca gaagtaagtt ggccgcagtg ttatcactca tggttatggc    9480
agcactgcat aattctctta ctgtcatgcc atccgtaaga tgcttttctg tgactggtga    9540
gtactcaacc aagtcattct gagaatagtg tatgcggcga ccgagttgct cttgcccggc    9600
gtcaatacgg gataataccg cgccacatag cagaacttta aaagtgctca tcattggaaa    9660
acgttcttcg gggcgaaaac tctcaaggat cttaccgctg ttgagatcca gttcgatgta    9720
acccactcgt gcacccaact gatcttcagc atctttttact ttcaccagcg tttctgggtg    9780
agcaaaaaca ggaaggcaaa atgccgcaaa aaagggaata agggcgacac ggaaatgttg    9840
aatactcata ctcttccttt ttcaatatta ttgaagcatt tatcagggtt attgtctcat    9900
gagcggatac atatttgaat gtatttagaa aaataaacaa atagggttc cgcgcacatt     9960
tccccgaaaa gtgccacctg acgtctaaga accattatt atcatgacat taacctataa    10020
aaataggcgt atcacgaggc cctttcgtct cgcgcgtttc ggtgatgacg gtgaaaacct   10080
ctgacacatg cagctcccgg agacggtcac agcttgtctg taagcggatg ccgggagcag   10140
acaagcccgt cagggcgcgt cagcgggtgt tggcgggtgt cggggctggc ttaactatgc   10200
ggcatcagag cagattgtac tgagagtgca ccatatggac atattgtcgt tagaacgcgg   10260
ctacaattaa tacataacct tatgtatcat acacatacga tttaggtgac actatagaac   10320
tcgagcagct g                                                        10331
```

SYNTHETIC PHYTASE VARIANTS

RELATED APPLICATIONS

This application is continuation of PCT/IB2012/051933 filed on Apr. 18, 2012, which claims benefit of U.S. Provisional Application Ser. No. 61/477,637 filed Apr. 21, 2011 and of European application 11163410.1 filed Apr. 21, 2011. The content of each of the above mentioned applications is hereby incorporated by reference in their entirety.

SEQUENCE LISTING SUBMISSION

The Sequence Listing associated with this application is filed in electronic format via EFS-Web and hereby incorporated by reference into the specification in its entirety. The name of the text file containing the Sequence Listing is Sequence_Listing_12810_01466_US. The size of the text file is 70 KB, and the text file was created on Nov. 20, 2012.

The present invention relates to phytases, to amino acid sequences coding for phytase enzymes and to nucleotide sequences which code for phytases, and to processes for the preparation and the use of phytases and to animal feeds comprising these phytases.

Phosphorus is an essential element for the growth of living organisms. In animal production, feed, as a rule, has to be supplemented with inorganic phosphorus in order to achieve good growth rates. In cereals and pulses, phosphorus is stored mainly in the form of phytate. However, monogastric animals such as pigs, poultry and fish are not capable of directly absorbing phytate or phytic acid, which results in the excretion of phytate, which means phosphorus overloads in regions with intensive livestock production. Furthermore, phytic acid, which binds metals such as calcium, copper or zinc, acts as a substance with a negative effect on the metabolism of monogastric animals. In order to compensate for the phosphate deficit of these animals and to ensure sufficient growth and sufficient health, inorganic phosphate is added to the animal feed. This addition of inorganic phosphate is costly and leads to a further adverse effect on the environment. By using a phytase in animal feeds, the phytate is hydrolyzed and results in a lower content of inositol phosphate and inorganic phosphates in the slurry. The addition of phytases to animal feeds improves the availability of organic phosphorus and reduces the adverse effect on the environment by excreted, phytate-bound phosphates. The literature describes a variety of natural phytases, both of fungal and of bacterial origin.

Phytases, also referred to as myo-inositol hexakisphosphate phosphohydrolase, are a class of phosphatases which are capable of cleaving at least one phosphate residue from phytate.

EP 420 358 generally describes the cloning and expression of microbial phytases, WO 2006/38062 describes microbial phytases derived from *Citrobacter freundii* as additive to animal feeds, and WO 2007/112739 describes phytases based on a natural phytase from *Citrobacter braakii* and processes for its preparation and the use in animal feeds.

Haefner et al. (Haefner S., Knietsch A., Scholten E., Braun J., Lohscheidt M. and Zelder O. (2005) Biotechnological production and application of phytases. Appl Microbiol Biotechnol 68:588-597) describe a multiplicity of known uses of phytases in the field of human or animal nutrition. Further uses of phytases such as, for example, the use for hydrolyzing biomass or starch in the production of bioethanol are described in WO 2008/097620.

WO 2008/116878 and WO 2010/034835 describe a phytase from *Hafnia alvei*, its protein sequence and variants thereof. Zinin et al. (FEMS Microbiology Letters (2004) 236: 283-290) disclose a phytase from *Obesumbacterium proteus*, whose sequence is deposited at the UNIPROT database with the accession number Q6U677. The patent applications WO 2006/043178, WO 2008/097619 and WO 2008/092901 describe phytases from various *Buttiauxella* sp. The natural phytases with the currently highest specific activities include the natural phytases from *Yersinia intermedia* (WO 2007/128160) and *Yersinia pestis* (WO 02/048332).

However, all of these currently available phytases do not show those properties which are required for the preparation of animal feed additives. The currently available phytases are not sufficiently thermally stable for being employed in the preparation of animal feed pellets without a considerable loss of their activity. In the preparation of animal feed pellets, phytase together with further customary animal feed components is compressed under high temperatures and humidity in order to be fed to the livestock as one entity. An effective destruction of *salmonella* sp. and the gelatinization of the starch is only achieved above a temperature of 80° C. during the preparation (Amerah et al. Worlds Poulty Science Journal (2011) 67:29-45). This compressing under hot and humid conditions results in considerable phytase activity losses. One possibility of preventing this loss of activity is the laborious coating of the phytase particles, so that they are protected against the effect of heat. This coating of the phytase additions causes considerable additional costs as the result of the fats or polymers employed for the coating. The doses of commercial phytases are usually determined on the basis of the activity determination at pH 5.5 (DIN ISO 30024:2009) and is not adapted to match the pH in the respective digestive tract. This results in considerable misdosages by variation of the activity at pH values other than 5.5.

It was therefore an object of the present invention to provide a phytase which has a sufficient thermal stability, so that it can be employed in the preparation of *salmonella*-free feed pellets without additional protective measures such as coating and with activity losses which are as low as possible. It was a further object of the invention to provide a phytase which can be employed over a wide pH range accompanied by as little reduction of the enzymatic activity as possible, so that it can be employed in the various pH ranges of the digestive tracts of different animal species and so that a sufficient enzymatic activity in the digestive tract is ensured even when the pH range fluctuates as the result of varying feed components.

These objects are achieved by a synthetic phytase which has an amino acid sequence with at least 85% identity to the amino acid sequence of SEQ ID 24. These phytases according to the invention have a thermostability of at least 80° C. and are therefore suitable for being employed in the preparation of feed pellets without suffering a considerable activity loss as the result of the hot and moist conditions during pelleting.

They furthermore have a broad pH range of over 3 pH units, within which they retain at least 50% of the activity determined at pH 5.5, so that, when the dosage is determined on the basis of the activity at 5.5, they can be employed in a multiplicity of animals with different digestive pH and together with different feed components, without an unduly low dosage resulting in activity losses and therefore to an increased excretion of the phosphate by the animals.

Furthermore, the phytase according to the invention surprisingly have an elevated proteolytic stability, and therefore they can pass through the stomach without substantial activity losses and the activity at the actual site of action, in the gut, is retained. Furthermore, the phytases according to the invention have a stability at pH 2 of at least 85% and thus ensure only small activity losses in the highly acidic range.

The synthetic phytase can also have an amino acid sequence with at least 90% identity to the amino acid sequence of SEQ ID 24.

Preferably, the synthetic phytase according to the invention has an amino acid sequence with at least 94%, in particular by preference 95% and preferably 96, 97, 98 or 99% identity to the amino acid sequence of SEQ ID 24.

The object is furthermore achieved by a synthetic phytase which has an amino acid sequence with at least 95%, by preference 96%, preferably 97, 98 or 99%, identity to the amino acid sequence of the mutant PhV-001 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-002 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-003 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-004 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-005 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-006 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-007 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-008 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-009 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-010 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-011 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-012 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-013 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-014 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-015 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-016 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-017 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-018 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-019 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-020 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-021 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-022 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-023 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-024 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-025 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-026 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-027 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-028 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-029 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-030 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-031 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-032 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-033 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-034 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-035 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-036 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-037 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-038 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-039 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-040 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-041 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-042 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-043 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-044 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-045 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-046 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-047 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-048 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-049 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-050 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-051 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-052 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-053 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-054 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-055 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-056 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-057 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-058 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-059 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-060 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-061 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-062 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-063 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-064 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-065 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-066 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-067 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-068 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-069 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-070 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-071 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-072 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-073 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-074 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-075 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-076 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-077 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-078 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-079 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-080 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-081 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-082 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-083 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-084 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-085 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-086 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-087 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-088 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-089 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-090 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-091 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-092 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-093 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-094 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-095 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-096 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-097 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-098 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-099 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-100 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-101 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-102 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-103 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-104 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-1105 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-106 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-107 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-109 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-110 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-111 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-112 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-113 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-114 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-115 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-116 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-117 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-118 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-119 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-120 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-121 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-122 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-123 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-124 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-125 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-126 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-127 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-128 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-129 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-130 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-131 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-132 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-133 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-134 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-135 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-136 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-137 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-138 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-139 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-140 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-141 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-142 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-143 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-144 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-145 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-146 (see Table 1, mutations as per column 2 based on SEQ ID 24).

The object is furthermore achieved by a synthetic phytase which has an amino acid sequence with at least 95%, by preference 96%, preferably 97, 98 or 99%, identity to the amino acid sequence of the mutant PhV-147 (see Table 1, mutations as per column 2 based on SEQ ID 24).

The identity between two protein sequences or nucleic acid sequences is defined as the identity calculated by the program needle in the version available in April 2011. Needle is part of the freely available program package EMBOSS, which can be downloaded from the website http://emboss.sourceforge.net/. The standard parameters are used: gapopen 10.0 ("gap open penalty"), gapextend 0.5 ("gap extension penalty"), datafile EBLOSUM62 (matrix) in the case of protein and datafile EDNAFULL (matrix) in the case of DNA.

In one embodiment, the synthetic phytase has at least one conservative amino acid exchange at at least one position compared with one of the above-described phytases according to the invention:

For the purposes of the present invention, conservative means an exchange of the amino acid G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R. Here, it is possible to combine any conservative exchange of an amino acid with any conservative exchange of another amino acid as long as the phytase activity is retained.

Advantageously, the synthetic phytase is an isolated phytase. It is also feasible that the synthetic phytase is present not as a purified isolated phytase, but as a fermentation liquor, with the biomass being separated off fully, partially or not at all. Here, the liquor can be concentrated or dried fully by removing liquid. It is possible to employ these unpurified or partially purified phytase solutions or phytase solids as additive in different products.

The synthetic phytase according to the invention advantageously has an elevated stability to pepsin, an improved acid stability at pH 2, a widening of the active pH range and/or an elevated thermostability compared with the two wild-type phytases from the organisms Yersinia mollaretii and Hafnia sp., which were the basis of the construction of the synthetic phytase construct of SEQ ID 18.

The invention also comprises an isolated nucleic acid sequence coding for a phytase with an amino acid sequence with at least 81%, advantageously 85 or 90%, especially preferably 94% and in particular 95, 96, 97, 98 or 99%, identity to the amino acid sequence of SEQ ID 24.

The invention likewise comprises an isolated nucleic acid sequence which codes for an enzyme with phytase activity, where the nucleic acid sequence has at least 85% identity to the nucleic acid sequence of SEQ ID 25, or a nucleic acid sequence which hybridizes under highly-stringent conditions with the complementary strand of one of the abovementioned sequences with at least 85% identity to the nucleic acid sequence of SEQ ID 25. In a particular embodiment, the isolated nucleic acid sequence has more than 90%, in particular at least 91, 92, 93, 94, 95, 96, 97, 98 or 99%, identity to SEQ ID 25.

The invention furthermore comprises a recombinant expression vector comprising one of the nucleic acid sequences according to the invention.

The invention likewise comprises a recombinant host cell comprising one of the nucleic acids according to the invention or comprising the recombinant expression vector according to the invention.

The object is furthermore achieved by a recombinant production organism, which is a nonhuman production organism which comprises one of the nucleic acid sequences according to the invention or which comprises the recombinant expression vector according to the invention. The recombinant production organism is especially preferably one from the genus *Aspergillus, Pichia, Trichoderma, Hansenula, Saccharomyces, Bacillus, Escherischia, Kluyveromyces, Schizosaccharomyces*.

The invention furthermore comprises an animal feed additive which comprises at least one of the phytases according to the invention, in particular with an amino acid sequence corresponding to SEQ ID 24 or one of the mutants PhV-001, PhV-002, PhV-003, PhV-004, PhV-005, PhV-006, PhV-007, PhV-008, PhV-009, PhV-010, PhV-011, PhV-012, PhV-013, PhV-014, PhV-015, PhV-016, PhV-017, PhV-018, PhV-019, PhV-020, PhV-021, PhV-022, PhV-023, PhV-024, PhV-025, PhV-026, PhV-027, PhV-028, PhV-029, PhV-030, PhV-031, PhV-032, PhV-033, PhV-034, PhV-035, PhV-036, PhV-037, PhV-038, PhV-039, PhV-040, PhV-041, PhV-042, PhV-043, PhV-044, PhV-045, PhV-046, PhV-047, PhV-048, PhV-049, PhV-050, PhV-051, PhV-052, PhV-053, PhV-054, PhV-055, PhV-056, PhV-057, PhV-058, PhV-059, PhV-060, PhV-061, PhV-062, PhV-063, PhV-064, PhV-065, PhV-066, PhV-067, PhV-068, PhV-069, PhV-070, PhV-071, PhV-072, PhV-073, PhV-074, PhV-075, PhV-076, PhV-077, PhV-078, PhV-079, PhV-080, PhV-081, PhV-082, PhV-083, PhV-084, PhV-085, PhV-086, PhV-087, PhV-088, PhV-089, PhV-090, PhV-091, PhV-092, PhV-093, PhV-094, PhV-095, PhV-096, PhV-097, PhV-098, PhV-099, PhV-100, PhV-101, PhV-102, PhV-103, PhV-104, PhV-105, PhV-106, PhV-107, PhV-109, PhV-110, PhV-111, PhV-112, PhV-113, PhV-114, PhV-115, PhV-116, PhV-117, PhV-118, PhV-119, PhV-120, PhV-121, PhV-122, PhV-123, PhV-124, PhV-125, PhV-126, PhV-127, PhV-128, PhV-129, PhV-130, PhV-131, PhV-132, PhV-133, PhV-134, PhV-135, PhV-136, PhV-137, PhV-138, PhV-139, PhV-140, PhV-141, PhV-142, PhV-143, PhV-144, PhV-145, PhV-146 or PhV-147 (according to the definition in Table 1) or with an amino acid sequence with at least 90, 91, 92, 93, 94, 95, 96, 97, 98 or 99% identity thereto, and furthermore customary feed additives, for example for cattle, poultry or pigs, such as, for example, vitamins, minerals or other additives.

The invention furthermore comprises an animal feed which comprises at least one of the described synthetic phytases according to the invention, in particular with an amino acid sequence corresponding to SEQ ID 24 or one of the mutants PhV-001, PhV-002, PhV-003, PhV-004, PhV-005, PhV-006, PhV-007, PhV-008, PhV-009, PhV-010, PhV-011, PhV-012, PhV-013, PhV-014, PhV-015, PhV-016, PhV-017, PhV-018, PhV-019, PhV-020, PhV-021, PhV-022, PhV-023, PhV-024, PhV-025, PhV-026, PhV-027, PhV-028, PhV-029, PhV-030, PhV-031, PhV-032, PhV-033, PhV-034, PhV-035, PhV-036, PhV-037, PhV-038, PhV-039, PhV-040, PhV-041, PhV-042, PhV-043, PhV-044, PhV-045, PhV-046, PhV-047, PhV-048, PhV-049, PhV-050, PhV-051, PhV-052, PhV-053, PhV-054, PhV-055, PhV-056, PhV-057, PhV-058, PhV-059, PhV-060, PhV-061, PhV-062, PhV-063, PhV-064, PhV-065, PhV-066, PhV-067, PhV-068, PhV-069, PhV-070, PhV-071, PhV-072, PhV-073, PhV-074, PhV-075, PhV-076, PhV-077, PhV-078, PhV-079, PhV-080, PhV-081, PhV-082, PhV-083, PhV-084, PhV-085, PhV-086, PhV-087, PhV-088, PhV-089, PhV-090, PhV-091, PhV-092, PhV-093, PhV-094, PhV-095, PhV-096, PhV-097, PhV-098, PhV-099, PhV-100, PhV-101, PhV-102, PhV-103, PhV-104, PhV-105, PhV-106, PhV-107, PhV-109, PhV-110, PhV-111, PhV-112, PhV-113, PhV-114, PhV-115, PhV-116, PhV-117, PhV-118, PhV-119, PhV-120, PhV-121, PhV-122, PhV-123, PhV-124, PhV-125, PhV-126, PhV-127, PhV-128, PhV-129, PhV-130, PhV-131, PhV-132, PhV-133, PhV-134, PhV-135, PhV-136, PhV-137, PhV-138, PhV-139, PhV-140, PhV-141, PhV-142, PhV-143, PhV-144, PhV-145, PhV-146 or PhV-147 (according to the definition in Table 1) or with an amino acid sequence with at least 90, 91, 92, 93, 94, 95, 96, 97, 98 or 99% identity thereto, together with customary feed components. Feasible feed components in this context are all those which are conventionally employed in feed pellets for beef, dairy cow, poultry or pig fattening.

The invention furthermore comprises the use of one of the described synthetic phytases according to the invention, in particular with an amino acid sequence corresponding to SEQ ID 24 or one of the mutants PhV-001, PhV-002, PhV-003, PhV-004, PhV-005, PhV-006, PhV-007, PhV-008, PhV-009, PhV-010, PhV-011, PhV-012, PhV-013, PhV-014, PhV-015, PhV-016, PhV-017, PhV-018, PhV-019, PhV-020, PhV-021, PhV-022, PhV-023, PhV-024, PhV-025, PhV-026, PhV-027, PhV-028, PhV-029, PhV-030, PhV-031, PhV-032, PhV-033, PhV-034, PhV-035, PhV-036, PhV-037, PhV-038, PhV-039, PhV-040, PhV-041, PhV-042, PhV-043, PhV-044, PhV-045, PhV-046, PhV-047, PhV-048, PhV-049, PhV-050, PhV-051, PhV-052, PhV-053, PhV-054, PhV-055, PhV-056, PhV-057, PhV-058, PhV-059, PhV-060, PhV-061, PhV-062, PhV-063, PhV-064, PhV-065, PhV-066, PhV-067, PhV-068, PhV-069, PhV-070, PhV-071, PhV-072, PhV-073, PhV-074, PhV-075, PhV-076, PhV-077, PhV-078, PhV-079, PhV-080, PhV-081, PhV-082, PhV-083, PhV-084, PhV-085, PhV-086, PhV-087, PhV-088, PhV-089, PhV-090, PhV-091, PhV-092, PhV-093, PhV-094, PhV-095, PhV-096, PhV-097, PhV-098, PhV-099, PhV-100, PhV-101, PhV-102, PhV-103, PhV-104, PhV-105, PhV-106, PhV-107, PhV-109, PhV-110, PhV-111, PhV-112, PhV-113, PhV-114, PhV-115, PhV-116, PhV-117, PhV-118, PhV-119, PhV-120, PhV-121, PhV-122, PhV-123, PhV-124, PhV-125, PhV-126, PhV-127, PhV-128, PhV-129, PhV-130, PhV-131, PhV-132, PhV-133, PhV-134, PhV-135, PhV-136, PhV-137, PhV-138, PhV-139, PhV-140, PhV-141, PhV-142, PhV-143, PhV-144, PhV-145, PhV-146 or PhV-147 (according to the definition in Table 1) or with an amino acid sequence with at least 90, 91, 92, 93, 94, 95, 96, 97, 98 or 99% identity thereto, in an animal feed. In this context, the use may take place in the form of the addition of the phytase according to the invention or of the animal feed additive according to the invention before the pelleting of the remaining feed components. It is also feasible to apply the phytase to these pellets after the preparation of feed pellets, in particular in liquid form.

The invention is furthermore achieved by the use of one of the above-described synthetic phytases according to the invention, in particular with an amino acid sequence corresponding to SEQ ID 24 or one of the mutants PhV-001, PhV-002, PhV-003, PhV-004, PhV-005, PhV-006, PhV-007, PhV-008, PhV-009, PhV-010, PhV-011, PhV-012, PhV-013, PhV-014, PhV-015, PhV-016, PhV-017, PhV-018, PhV-019, PhV-020, PhV-021, PhV-022, PhV-023, PhV-024, PhV-025, PhV-026, PhV-027, PhV-028, PhV-029, PhV-030, PhV-031, PhV-032, PhV-033, PhV-034, PhV-035, PhV-036, PhV-037, PhV-038, PhV-039, PhV-040, PhV-041, PhV-042, PhV-043, PhV-044, PhV-045, PhV-046, PhV-047, PhV-048, PhV-049, PhV-050, PhV-051, PhV-052, PhV-053, PhV-054, PhV-055, PhV-056, PhV-057, PhV-058, PhV-059, PhV-060, PhV-061, PhV-062, PhV-063, PhV-064, PhV-065, PhV-066, PhV-067, PhV-068, PhV-069, PhV-070, PhV-071, PhV-072, PhV-073, PhV-074, PhV-075, PhV-076, PhV-077, PhV-078, PhV-079, PhV-080, PhV-081, PhV-082, PhV-083, PhV-084, PhV-085, PhV-086, PhV-087, PhV-088, PhV-089, PhV-090, PhV-091, PhV-092, PhV-093, PhV-094, PhV-095, PhV-096, PhV-097, PhV-098, PhV-099, PhV-100, PhV-101, PhV-102, PhV-103, PhV-104, PhV-105, PhV-106, PhV-107, PhV-109, PhV-110, PhV-111, PhV-112, PhV-113, PhV-114, PhV-115, PhV-116, PhV-117, PhV-118, PhV-119, PhV-120, PhV-121, PhV-122, PhV-123, PhV-124, PhV-125, PhV-126, PhV-127, PhV-128, PhV-129, PhV-130, PhV-131, PhV-132, PhV-133, PhV-134, PhV-135, PhV-136, PhV-137, PhV-138, PhV-139, PhV-140, PhV-141, PhV-142, PhV-143, PhV-144, PhV-145, PhV-146 or PhV-147 (according to the definition in Table 1) or with an amino acid sequence with at least 90, 91, 92, 93, 94, 95, 96, 97, 98 or 99% identity thereto, of the animal feed additive according to the invention, which comprises at least one of the synthetic phytases according to the invention, in particular with an amino acid sequence corresponding to SEQ ID 24 or one of the mutants PhV-001, PhV-002, PhV-003, PhV-004, PhV-005, PhV-006, PhV-007, PhV-008, PhV-009, PhV-010, PhV-011, PhV-012, PhV-013, PhV-014, PhV-015, PhV-016, PhV-017, PhV-018, PhV-019, PhV-020, PhV-021, PhV-022, PhV-023, PhV-024, PhV-025, PhV-026, PhV-027, PhV-028, PhV-029, PhV-030, PhV-031, PhV-032, PhV-033, PhV-034, PhV-035, PhV-036, PhV-037, PhV-038, PhV-039, PhV-040, PhV-041, PhV-042, PhV-043, PhV-044, PhV-045, PhV-046, PhV-047, PhV-048, PhV-049, PhV-050, PhV-051, PhV-052, PhV-053, PhV-054, PhV-055, PhV-056, PhV-057, PhV-058, PhV-059, PhV-060, PhV-061, PhV-062, PhV-063, PhV-064, PhV-065, PhV-066, PhV-067, PhV-068, PhV-069, PhV-070, PhV-071, PhV-072, PhV-073, PhV-074, PhV-075, PhV-076, PhV-077, PhV-078, PhV-079, PhV-080, PhV-081, PhV-082, PhV-083, PhV-084, PhV-085, PhV-086, PhV-087, PhV-088, PhV-089, PhV-090, PhV-091, PhV-092, PhV-093, PhV-094, PhV-095, PhV-096, PhV-097, PhV-098, PhV-099, PhV-100, PhV-101, PhV-102, PhV-103, PhV-104, PhV-105, PhV-106, PhV-107, PhV-109, PhV-110, PhV-111, PhV-112, PhV-113, PhV-114, PhV-115, PhV-116, PhV-117, PhV-118, PhV-119, PhV-120, PhV-121, PhV-122, PhV-123, PhV-124, PhV-125, PhV-126, PhV-127, PhV-128, PhV-129, PhV-130, PhV-131, PhV-132, PhV-133, PhV-134, PhV-135, PhV-136, PhV-137, PhV-138, PhV-139, PhV-140, PhV-141, PhV-142, PhV-143, PhV-144, PhV-145, PhV-146 or PhV-147 (according to the definition in Table 1) or with an amino acid sequence with at least 90, 91, 92, 93, 94, 95, 96, 97, 98 or 99% identity thereto, or of the animal feed which comprises at least one of the described synthetic phytases, in particular with an amino acid sequence corresponding to SEQ ID 24 or one of the mutants PhV-001, PhV-002, PhV-003, PhV-004, PhV-005, PhV-006, PhV-007, PhV-008, PhV-009, PhV-010, PhV-011, PhV-012, PhV-013, PhV-014, PhV-015, PhV-016, PhV-017, PhV-018, PhV-019, PhV-020, PhV-021, PhV-022, PhV-023, PhV-024, PhV-025, PhV-026, PhV-027, PhV-028, PhV-029, PhV-030, PhV-031, PhV-032, PhV-033, PhV-034, PhV-035, PhV-036, PhV-037, PhV-038, PhV-039, PhV-040, PhV-041, PhV-042, PhV-043, PhV-044, PhV-045, PhV-046, PhV-047, PhV-048, PhV-049, PhV-050, PhV-051, PhV-052, PhV-053, PhV-054, PhV-055, PhV-056, PhV-057, PhV-058, PhV-059, PhV-060, PhV-061, PhV-062, PhV-063, PhV-064, PhV-065, PhV-066, PhV-067, PhV-068, PhV-069, PhV-070, PhV-071, PhV-072, PhV-073, PhV-074, PhV-075, PhV-076, PhV-077, PhV-078, PhV-079, PhV-080, PhV-081, PhV-082, PhV-083, PhV-084, PhV-085, PhV-086, PhV-087, PhV-088, PhV-089, PhV-090, PhV-091, PhV-092, PhV-093, PhV-094, PhV-095, PhV-096, PhV-097, PhV-098, PhV-099, PhV-100, PhV-101, PhV-102, PhV-103, PhV-104, PhV-105, PhV-106, PhV-107, PhV-109, PhV-110, PhV-111, PhV-112, PhV-113, PhV-114, PhV-115, PhV-116, PhV-117, PhV-118, PhV-119, PhV-120, PhV-121, PhV-122, PhV-123, PhV-124, PhV-125, PhV-126, PhV-127, PhV-128, PhV-129, PhV-130, PhV-131, PhV-132, PhV-133, PhV-134, PhV-135, PhV-136, PhV-137, PhV-138, PhV-139, PhV-140, PhV-141, PhV-142, PhV-143, PhV-144, PhV-145, PhV-146 or PhV-147 (according to the definition in Table 1) or with an amino acid sequence with at least 90, 91, 92, 93, 94, 95, 96, 97, 98 or 99% identity thereto, for reducing the phosphate content in the slurry of livestock.

The embodiments described are intended to illustrate and to give a better understanding of the invention and are in no way to be construed as limiting. Further features of the invention result from the description hereinbelow of preferred embodiments in conjunction with the dependent claims. In this context, the individual features of the invention may, in one embodiment, be realized in each case individually or together and are no limitation whatsoever of the invention to the described embodiment. The wording of the patent claims is hereby expressly made subject matter of the description.

EXAMPLES

Figure 1:
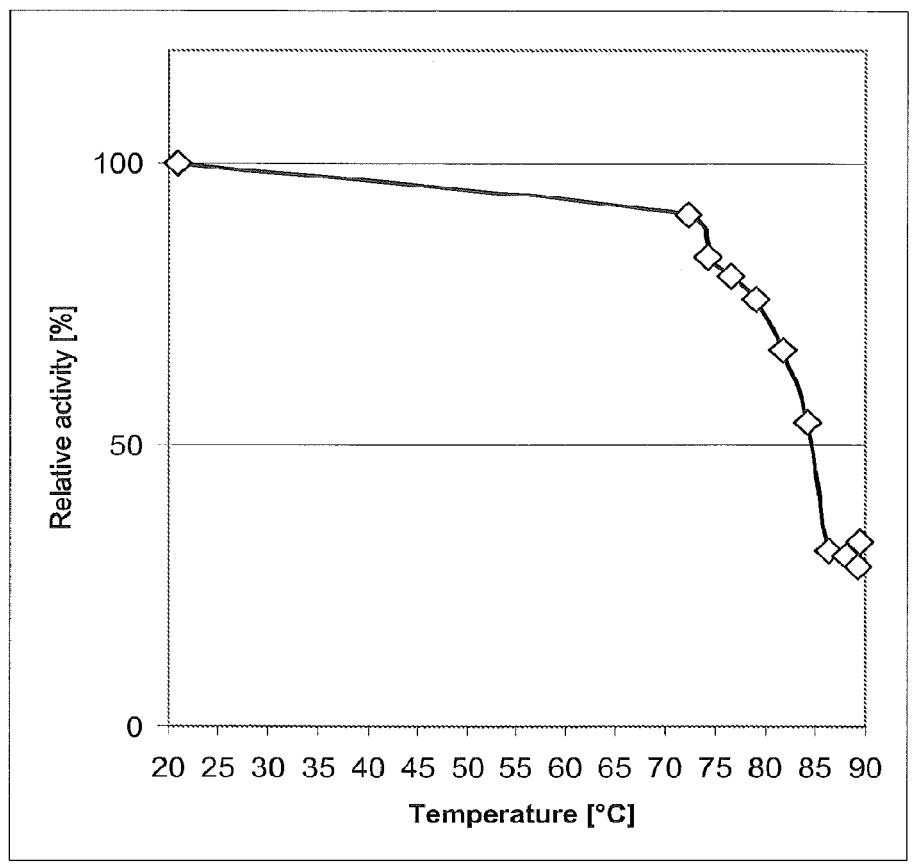
FIG. 1 shows the thermostability of the phytase HF598 (SEQ ID 24). The phytase is heated for 20 min at pH 5.5 at the temperature stated. After cooling, the residual activity at pH 5.5 and 37° C. is determined. To determine the relative residual activity, the activity of a reference sample incubated for 20 min at room temperature is set at 100%.

Cloning the Phytase from *Hafnia* sp. LU11047

Phytases are searched for in a series of enterobacteria analogously to the publications Huang et al. (2006) A novel phytase with preferable characteristics from *Yersinia intermedia*. Biochem Biophys Res Commun 350: 884-889, Shi et al. (2008) A novel phytase gene appA from *Buttiauxella* sp. GC21 isolated from grass carp intestine. Aquaculture 275:70-75 und WO2008116878 (Example 1) with the aid of the degenerate oligos Haf1090 5'-GAYCCNYTNTTYCAYCC-3' (SEQ ID: 1) and Haf1092 5'-GGNGTRTTRTCNGGYTG-3' (SEQ ID: 2) at annealing temperatures of between 40° C. and 50° C., using PCR. The PCR products formed are employed as template for a semi-nested PCR using the oligos Haf1090 5'-GAYCCNYTNTTYCAYCC-3' (SEQ ID 1) and Haf1091 5'-GCDATRTTNGTRTCRTG-3' (SEQ ID 3) under identical annealing conditions. A fragment can be isolated from a bacterial strain of the genus *Hafnia* (*Hafnia* sp. LU11047). The isolated fragment is subcloned with the aid of the "TOPO TA Cloning® Kit" (Invitrogen) following the manufacturer's instructions and subsequently sequenced. Starting from this part-sequence, the full-length sequence of the phytase is amplified via the so-called TAIL-PCR method (Yao-Guang Liu and Robert F. Whittier (1995) Thermal asymmetric interlaced PCR: automatable amplification and sequencing of insert end fragments from P1 and YAC clones for chromosome walking. Genomics 25, 674-681). The following oligonucleotides are used for this purpose:

```
Amplification of the 3' end:
1. Haf1165 (5'-WCAGNTGWTNGTCVTG-3', SEQ ID 4)
   and
   Haf1167 (5'-CTTCGAGAGCCACTTTATTACCGTCG-3',
            (SEQ ID 5)

2. Haf1165 (5'-WCAGNTGWTNGTNCTG-3' SEQ ID 4)
   and
   Haf1168 (5'-CCAATGTTGTGCTGCTGACAATAGG-3',
            SEQ ID 6)

3. Haf1165 (5'-WCAGNTGWTNGTNCTG-3', SEQ ID 4)
   and
   Haf1169 (5'-
            CCGAACTCATCAGCGCTAAAGATGC-
            3', SEQ ID 7)

Amplification of the 5' end:
1. Haf1077 (5'-CAWCGWCNGASASGAA-3', SEQ ID 8)
   and
   Haf1170 (5'-CGCAGTTTGACTTGATGTCGCGCACG-3',
            SEQ ID 9)

2. Haf1077 (5'-CAWCGWCNGASASGAA-3', SEQ ID 8)
   and
   Haf1171 (5'-GTCGCGCACGCCCTATATCGCCAAGC-3',
            SEQ ID 10)

3. Haf1077 (5'-CAWCGWCNGASASGAA-3', SEQ ID 8)
   and
   Haf1172 (5'-CTGCAAACCATCGCACACGCACTGG-3',
            SEQ ID 11)
```

The DNA fragments obtained are cloned with the aid of the "TOPO TA Cloning® Kit" (Invitrogen) and sequenced. The nucleotide sequences give the gene SEQ ID 12, which codes for the *Hafnia* sp. LU11047 phytase. The amino acid sequence SEQ ID 13, which is derived therefrom, has 98% identity with the phytase sequence of a *Hafnia alvei* phytase from WO200811678. Using the software SignalP 2.0, the amino acids 1-33 are predicted to be a signal peptide. The mature enzyme, accordingly, starts with the serine in position 34.

1. Synthetic Phytase Fus5#2
Cloning the Phytase Fus5#2

Starting from the chromosomal DNA from *Hafnia* sp. LU11047, a fragment of base 1-1074 of the phytase (SEQ ID 14) is amplified by means of PCR. Oligonucleotides are derived from the DNA sequence of a putative phytase (or acidic phosphatase) from *Yersinia mollaretii* ATCC43969, NCBI Sequenz ID ZP_00824387 for amplifying the nucleotides 1057-1323. This is used to amplify a second phytase fragment from the chromosomal DNA from *Yersinia mollaretii* ATCC 43969 (SEQ ID 15). Upon amplification of the two phytase fragments, an overlap of 20 bp to the respective other phytase fragment is generated, with the aid of the oligos used, both at the 3' end of the *Hafnia* fragment and at the 5' end of the *Yersinia* fragment. In this manner, the two fragments can be combined via PCR fusion to give the phytase sequence SEQ ID 16, which codes for the synthetic phytase Fus5#2. For the amino acid sequence SEQ ID 17 derived therefrom, the amino acids 1-33 are predicted by the software SignalP 2.0 to be a signal peptide. The mature phytase Fus5#2 (SEQ ID 18) is encoded by the nucleotide sequence SEQ ID 19.

To clone an expression plasmid for *E. coli*, an NdeI restriction cleavage site is generated at the 5' end of the phytase DNA fragment SEQ ID 16 and a HindIII restriction cleavage site and a stop codon are generated at the 3' end. The sequences additionally required for this are introduced by means of a PCR reaction via the primers used, with the aid of the phytase SEQ ID 16 as the template. Using these cleavage sites, the phytase-encoding gene is cloned into the *E. coli* expression vector pET22b (Novagen). By using the NdeI restriction cleavage site and by introducing the stop codon, the pelB signal sequence is removed from the vector and read-through into the 6xHis tag, which is present on the plasmid, is prevented. The plasmid pFus5#2 (SEQ ID 20) thus generated is transformed into the *E. coli* strain BL21 (DE3) (Invitrogen). For the improved purification of the phytase protein, a phytase variant with an N-terminal 6xHis tag is cloned. Using the sense oligo primerH6: 5'-ctatggatccgcatcatcatcatcatcacagtgataccgcccctgc-3' (SEQ ID 21), which introduces not only the 6xHis tag, but also a BamHI cleavage site, and which acts as a template for the sequence SEQ ID 19, which codes for the mature phytase protein, a PCR product is amplified. At the 3' end of the PCR product, a stop codon and an NdeI restriction cleavage site are, again, introduced using the same antisense oligo. The fragment thus generated is cloned into the vector pET22b via BamHI/NdeI, giving rise to the plasmid pH6-Fus5#2 (SEQ ID 22), which is likewise transformed into *E. coli* BL21(DE3). In the case of this construct, the pelB signal sequence, which is comprised in pET22b, is used for the transport into the periplasma.

Phytase Assay

The phytase activity is determined in microtiter plates. The enzyme sample is diluted in reaction buffer (250 mM Na acetate, 1 mM $CaCl_2$, 0.01% Tween 20, pH 5.5). 10 μl of the enzyme solution are incubated with 140 μl substrate solution (6 mM Na phytate (Sigma P3168) in reaction buffer) for 1 h at 37° C. The reaction is quenched by adding 150 μl of trichloroacetic acid solution (15% w/w). To detect the liberated phosphate, 20 μl of the quenched reaction solution are treated with 280 μl of freshly made-up color reagent (60 mM L-ascorbic acid (Sigma A7506), 2.2 mM ammonium molybdate tetrahydrate, 325 mM $H_2SO_4$), and incubated for 25 min at 50° C., and the absorption at 820 nm was subsequently determined. For the blank value, the substrate buffer on its own is incubated at 37° C. and the 10 μl of enzyme sample are only added after quenching with trichloroacetic acid. The color reaction is performed analogously to the remaining measurements. The amount of liberated phosphate is determined via a calibration curve of the color reaction with a phosphate solution of known concentration.

Expression in Escherichia coli

The E. coli BL21(DE3) strains, which harbor a plasmid with a phytase expression cassette, are grown at 37° C. in LB medium supplemented with ampicillin (100 mg/l). The phytase expression is induced at an OD (600 nm) of 0.6 by adding 1 mM IPTG. After 4 h of induction, 10% (v/v) of a 10× BugBuster solution (Novogen) is added and the mixture is incubated for 15 min at room temperature. After the centrifugation, the supernatant is used for determining the phytase activity.

Purification Via Ni Affinity Chromatography

To purify the 6×His-labeled phytase variants, an induced, phytase-expressing E. coli culture broth is treated with 300 mM NaCl, Complete™ Protease Inhibitor without EDTA (following the instructions of the manufacturer Roche Applied Science) and with 10% (v/v) of a 10× BugBuster solution (Novogen), and the mixture is incubated for 15 min at room temperature. After the centrifugation, the supernatant is bound to Ni-NTA columns/KIT (Qiagen) following the manufacturer's instructions. The elution after the wash steps is performed using cold elution buffer (50 mM Na acetate buffer, 300 mM NaCl, 500 mM imidazole, 1 mM $CaCl_2$). Before determining the protein content, the sample is subjected to a buffer exchange for 2 mM sodium citrate pH 5.5 by dialysis.

Expression in Aspergillus niger

To express the phytase Fus5#2 in Aspergillus niger, an expression construct is first prepared which comprises the phytase gene under the control of the A. niger glucoamylase (glaA) promoter, flanked by the noncoding 3'-glaA region. In this manner, the construct is intended for integration into the 3'-glaA region in A. niger. The signal sequence used for the extracellular protein secretion is the signal sequence of the A. ficuum phytase. The base used for the expression construct is the Plasmid pGBGLA-53 (also referred to as pGBTOPFYT-1 in WO9846772), which is described in detail in EP0635574B1. With the aid of PCR-based cloning techniques known to a person skilled in the art, the gene segment of the A. ficuum phytase, which codes for the mature phytase protein starting with the amino acid sequence ASRNQSS, in pGBGLA-53 is replaced by the gene segment SEQ ID 19, which codes for the mature Fus5#2 phytase. This gives rise to the resulting plasmid pGLA53-Fus5#2 (SEQ ID 23). The cotransformation of the linear expression cassette, isolated from the resulting plasmid using HindIII, together with an amdS marker cassette, isolated from the plasmid pGBLA50 (EP0635574B1)/pGBAAS-1 (name of the same plasmid in WO9846772), into a glaA-deleted A. niger expression strain and the subsequent expression of the phytase in shake flasks is performed as described in the two cited patent specifications. The phytase activity in the culture supernatant is determined daily after the cells have been centrifuged off. The maximum activity is achieved between day 3 and day 6.

2. Phytase Variants of Phytase Fus5#2

Variants of the phytase are generated by mutating the gene sequence SEQ ID 19 by means of PCR. The "Quickchange Site-directed Mutagenesis Kit" (Stratagene) is used to carry out a directed mutagenesis. A random mutagenesis over the entire coding sequence, or else only part thereof, of SEQ ID 19 is performed with the aid of the "GeneMorph II Random Mutagenesis Kit" (Stratagene). The mutagenesis rate is set to the desired amount of 1-5 mutations via the amount of the template DNA used. Multiple mutations are generated by the targeted combination of individual mutations or by the sequential performance of several mutagenesis cycles.

The phytase variants generated are tested for phytase activity and thermostability in an assay with high-throughput capability. To this end, the E. coli BL21(DE3) clones obtained after the transformation with the pET22b-based expression construct are incubated (30° C., 900 rpm, shaker excursion 2 mm) in 96-well microtiter plates in LB Medium (2% glucose, 100 mg/l ampicillin). Induction is carried out with 1 mM IPTG for 4 h at an OD (600 nm) of approximately 0.5. Thereafter, 10% (v/v) of a 10× BugBuster solution (Novogen) is then added and the mixture is incubated for 15 min at room temperature. The phytase activity and the residual activity after 20 minutes of temperature stress are determined.

The phytase HF598 (SEQ ID 24) generated in this manner and variants thereof are cloned into the E. coli expression vector pET22b (Novagen) analogously to the procedures described in the previous section and subsequently expressed with the aid of the E. coli strain BL21(DE3). In addition, suitable expression constructs for Aspergillus niger are cloned so that the phytase can be expressed after transformation into A. niger. When using a synthetic gene (SEQ ID 25), which codes for the mature variant HF598 (SEQ ID 24) and which had been adapted to the codon usage of A. niger (GENEART AG, Regensburg), the plasmid pGla53-HF598 (SEQ ID 26) is obtained.

Determination of the Thermostability ($T_{50}$)

To record the thermal inactivation curve, the enzyme sample which is diluted in reaction buffer (250 mM Na acetate, 1 mM $CaCl_2$, 0.01% Tween 20, pH 5.5) is heated for 20 min at the respective temperatures and thereafter cooled to 4° C. A reference sample which has not undergone thermal treatment is left at room temperature for 20 min and is then likewise cooled to 4° C. After the thermal pretreatment, the enzyme activity of the samples is determined by means of the phytase assay. The activity of the reference sample is normalized to 100%. The thermostability of the various phytase variants is characterized by what is known as the $T_{50}$ value. The $T_{50}$ indicates the temperature at which 50% residual activity is still present after thermal inactivation, compared with a reference sample which has not undergone thermal treatment. Changes in the thermostability of two phytase variants, expressed in ° C., result from the difference of the respective $T_{50}$ values.

TABLE 1

Thermostability ($T_{50}$) of the phytase HF598 (see FIG. 1) and its variants in ° C. Changes over SEQ ID 24 are specified at individual amino acid exchanges in the form [original amino acid][position4][new amino acid]. The symbol "—" indicates a deletion of the amino acid in question. The numbering of the amino acid position always refers to SEQ ID 24.

| Mutant | Mutation | $T_{50}$ [° C.] |
| --- | --- | --- |
| HF598 | SEQ ID 24 | 84 |
| PhV-001 | D2E A4E A6S F8Y D33M K76N N78T E144A G217S D398E | 84 |
| PhV-002 | D2E A4E A6S F8Y D33M K76N N78T N92A E144A G217S D398E | 85 |
| PhV-003 | D2E A4E A6S F8Y D33M R67L K76N N78T N92A E144A G217S M260I D398E | 85 |
| PhV-004 | D2E A4E A6S F8Y D33M R67L K76N N78T Q109N Q159N M260I D398E | 85 |
| PhV-005 | D33N P75N D77T V123A E144A G152T G217S | 81 |
| PhV-006 | D33N Q71E T121Q V123A E144A G152T G217S | 81 |
| PhV-007 | S1— D2— T3Q A4G P5A A6D G7K F8M Q9K K12R D33N K76N N78T V123A E144A G152T G217S | 81 |
| PhV-008 | D33N T121Q V123A S136K E144A G152T G217S Q406K | 81 |
| PhV-009 | S1— D2— T3Q A4G P5A A6D G7K F8M Q9K K12R D33M H37Y K76N N78T V123A E144A G152T G217S | 81 |
| PhV-010 | S1— D2— T3Q A4G P5A A6D G7K F8M Q9K K12R D33M K76N N78T V123A E144A G152T G217S | 82 |
| PhV-011 | S1— D2— T3Q A4G P5A A6D G7K F8M Q9K K12R D33M H37Y P75N D77T V123A E144A G152T G217S | 81 |
| PhV-012 | S1— D2— T3Q A4G P5A A6D G7K F8M Q9K K12R D33M K76N N78T V123A E144A G152T G217S D398E | 82 |
| PhV-013 | S1— D2— T3Q A4G P5A A6D G7K F8M Q9K K12R D33M K76N N78T V123A E144A G152T G217S D398K | 81 |
| PhV-014 | S1— D2— T3Q A4G P5A A6D G7K F8M Q9K K12R D33N K76N N78T V123A E144A G152T G217S D398G | 81 |
| PhV-015 | S1— D2— T3Q A4G P5A A6D G7K F8M Q9K K12R D33N K76N N78T Q109E V123A E144A G152T G217S | 81 |
| PhV-016 | S1— D2— T3Q A4G P5A A6D G7K F8M Q9K K12R D33N K76N N78T Q109N V123A E144A G152T G217S | 81 |
| PhV-017 | S1— D2— T3Q A4G P5A A6D G7K F8M Q9K K12R D33M K76N N78T V123A E144A G152T Q159N G217S | 82 |
| PhV-018 | S1— D2— T3Q A4G P5A A6D G7K F8M Q9K K12R D33M K76N N78T V123A E144A G152T G217S T322Q | 81 |
| PhV-019 | S1— D2— T3Q A4G P5A A6D G7K F8M Q9K K12R D33M K76N N78T V123A E144A G152A G217S | 82 |
| PhV-020 | S1— D2— T3Q A4G P5A A6D G7K F8M Q9K K12R D33M K76N N78T V123A E144A G217S | 83 |
| PhV-021 | S1— D2— T3Q A4G P5A A6D G7K F8M Q9K K12R D33M V123A E144A G152T G217S | 82 |
| PhV-022 | S1— D2— T3Q A4G P5A A6D G7K F8M Q9K K12R D33N K76N N78T V123A E144A G217S | 82 |
| PhV-023 | S1— D2— T3Q A4G P5A A6D G7K F8M Q9K K12R D33N K76N N78T V123A E144A G152T G217S I300L | 82 |
| PhV-024 | S1— D2— T3Q A4G P5A A6D G7K F8M Q9K K12R D33M K76N N78T V123A S136K Q141K E144A G152T G217S | 82 |
| PhV-025 | S1— D2— T3Q A4G P5A A6D G7K F8M Q9K K12R D33M K76N N78T V123A S136K E144A G152T G217S | 81 |
| PhV-026 | S1— D2— T3Q A4G P5A A6D G7K F8M Q9K K12R D33M K76N 77SQD79 V123A E144A G152T G217S | 82 |
| PhV-027 | S1— D2— T3Q A4G P5A A6D G7K F8M Q9K K12R D33M K76N 77SQG79 V123A E144A G152T G217S | 81 |
| PhV-028 | S1— D2— T3Q A4G P5A A6D G7K F8M Q9K K12R D33M K76N N78T V123A S136K E144A G152T A166E G217S | 81 |
| PhV-029 | S1— D2— T3Q A4G P5A A6D G7K F8M Q9K K12R D33M K76N N78T V123A S136K E144A G152T A166H G217S | 81 |
| PhV-030 | S1— D2— T3Q A4G P5A A6D G7K F8M Q9K K12R D33M K76N N78T V123A S136K E144A G152T | 82 |
| PhV-031 | D2E A4E A6S F8Y D33M K76N N78T V123A E144A G152T G217S | 83 |
| PhV-032 | S1— D2— T3Q A4G P5A A6D G7K F8M Q9K K12R D33M K76N N78T V123A E144A G152T N159K G217S | 81 |
| PhV-033 | S1— D2— T3Q A4G P5A A6D G7K F8M Q9K K12R D33M K76N N78T V123A E144A G152T G217S Q406K | 81 |
| PhV-034 | S1— D2— T3Q A4G P5A A6D G7K F8M Q9K K12R D33N K76N N78T E144A G152T G217S | 81 |
| PhV-035 | S1— D2— T3Q A4G P5A A6D G7K F8M Q9K K12R D33N K76N N78T E144A G152T G217S I300L | 81 |

TABLE 1-continued

*Thermostability ($T_{50}$) of the phytase HF598 (see FIG. 1) and its variants in ° C. Changes over SEQ ID 24 are specified at individual amino acid exchanges in the form [original amino acid][position4][new amino acid]. The symbol "—" indicates a deletion of the amino acid in question. The numbering of the amino acid position always refers to SEQ ID 24.*

| Mutant | Mutation | $T_{50}$ [° C.] |
|---|---|---|
| PhV-036 | S1— D2— T3Q A4G P5A A6D G7K F8M Q9K K12R D33M K76N N78T V123A G152T A166E G217S | 82 |
| PhV-037 | S1— D2— T3Q A4G P5A A6D G7K F8M Q9K K12R D33M K76N N78T V123A G152T A166H G217S | 82 |
| PhV-038 | S1— D2— T3Q A4G P5A A6D G7K F8M Q9K K12R D33M K76N N78T V123A G152T | 82 |
| PhV-039 | S1— D2— T3Q A4G P5A A6D G7K F8M Q9K K12R D33M K76N N78T V123A E144A G152T A166H G217S D398E | 82 |
| PhV-040 | S1— D2— T3Q A4G P5A A6D G7K F8M Q9K K12R D33M K76N N78T V123A E144A G152T D398E | 82 |
| PhV-041 | S1— D2— T3Q A4G P5A A6D G7K F8M Q9K K12R D33M K76N N78T V123A S136K E144A G152T G217S D398E | 82 |
| PhV-042 | S1— D2— T3Q A4G P5A A6D G7K F8M Q9K K12R D33M K76N N78T V123A S136K E144A G152T Q193L G217S | 82 |
| PhV-043 | S1— D2— T3Q A4G P5A A6D G7K F8M Q9K K12R D33M K76N N78T N119A V123A E144A G152T G217S | 81 |
| PhV-044 | S1— D2— T3Q A4G P5A A6D G7K F8M Q9K K12R D33M K76N N78T N119T V123A E144A G152T G217S | 81 |
| PhV-045 | S1— D2— T3Q A4G P5A A6D G7K F8M Q9K K12R D33M K76N N78T Q109N V123A E144A G217S I300L | 83 |
| PhV-046 | S1— D2— T3Q A4G P5A A6D G7K F8M Q9K K12R D33M K76N N78T Q109N V123A E144A G217S K268N I300L | 81 |
| PhV-047 | S1— D2— T3Q A4G P5A A6D G7K F8M Q9K K12R D33M K76N N78T Q109N V123A E144A G152T G217S K268N I300L | 81 |
| PhV-048 | S1— D2— T3Q A4G P5A A6D G7K F8M Q9K K12R D33M K76I N78T V123A E144A G217S | 83 |
| PhV-049 | S1— D2— T3Q A4G P5A A6D G7K F8M Q9K K12R D33M K76R N78T V123A E144A G217S | 82 |
| PhV-050 | S1— D2— T3Q A4G P5A A6D G7K F8M Q9K K12R D33M K76D N78T V123A E144A G217S | 82 |
| PhV-051 | S1— D2— T3Q A4G P5A A6D G7K F8M Q9K K12R D33M K76N N78T Q118S V123A E144A G152T G217S | 82 |
| PhV-052 | S1— D2— T3Q A4G P5A A6D G7K F8M Q9K K12R D33M K76N N78T Q118S N119A V123A E144A G152T G217S | 81 |
| PhV-053 | S1— D2— T3Q A4G P5A A6D G7K F8M Q9K K12R D33M K76N N78T E144A G217S I300L | 83 |
| PhV-054 | S1— D2— T3Q A4G P5A A6D G7K F8M Q9K K12R D33M K76N N78T Q118S N119A V123A E144A G217S | 82 |
| PhV-055 | D2E A4E A6S F8Y D33M K76N N78T V123A E144A G217S Q276N | 83 |
| PhV-056 | D2E A4E A6S F8Y D33M K76N N78T V123A E144A G152T G217S Q276N N346G | 82 |
| PhV-057 | S1— D2— T3Q A4G P5A A6D G7K F8M Q9K K12R D33M K76N N78T Q109N V123A E144A G217S Q276N I300L N346G | 82 |
| PhV-058 | D2E A4E A6S F8Y D33M K76N N78T V123A E144A G217S | 83 |
| PhV-059 | D2E A4E A6S F8Y D33M K76N N78T V123A E144A G217S D398E | 83 |
| PhV-060 | S1— D2— T3Q A4G P5A A6D G7K F8M Q9K K12R D33M K76N N78T Q109N V123A E144A G217S I300L N346G | 83 |
| PhV-061 | S1— D2— T3Q A4G P5A A6D G7K F8M Q9K K12R D33M K76N N78T V123A E144A G152T E155N G217S D345G | 81 |
| PhV-062 | S1— D2— T3Q A4G P5A A6D G7K F8M Q9K K12R D33M K76N N78T S136K E144A G217S | 82 |
| PhV-063 | S1— D2— T3Q A4G P5A A6D G7K F8M Q9K K12R D33N K76N N78T V123A E144A G152T E155N G217S Q276N | 82 |
| PhV-064 | S1— D2— T3Q A4G P5A A6D G7K F8M Q9K K12R D33N K76N N78T N92A V123A E144A G152T G217S | 84 |
| PhV-065 | S1— D2— T3Q A4G P5A A6D G7K F8M Q9K K12R D33N K76N N78T N92T V123A E144A G152T G217S | 83 |
| PhV-066 | S1— D2— T3Q A4G P5A A6D G7K F8M Q9K K12R D33N K76N N78T N92V V123A E144A G152T G217S | 83 |
| PhV-067 | S1— D2— T3Q A4G P5A A6D G7K F8M Q9K K12R D33N K76N N78T N92A E144A G152T G217S | 85 |
| PhV-068 | S1— D2— T3Q A4G P5A A6D G7K F8M Q9K K12R D33N K76N N78T N92E E144A G152T G217S | 84 |
| PhV-069 | S1— D2— T3Q A4G P5A A6D G7K F8M Q9K K12R D33N K76N N78T N92T E144A G152T G217S | 84 |
| PhV-070 | S1— D2— T3Q A4G P5A A6D G7K F8M Q9K K12R D33N K76N N78T N92V E144A G152T G217S | 85 |
| PhV-071 | S1A D2S T3R A4N P5A A6D G7K F8M Q9K K12R D33N K76N N78T V123A E144A G152T G217S | 83 |
| PhV-072 | S1— D2— T3Q A4G P5A A6D G7K F8M Q9K K12R D33N K76N N78T N92E V123A E144A G152T G217S | 84 |

TABLE 1-continued

*Thermostability ($T_{50}$) of the phytase HF598 (see FIG. 1) and its variants in ° C. Changes over SEQ ID 24 are specified at individual amino acid exchanges in the form [original amino acid][position4][new amino acid]. The symbol "—" indicates a deletion of the amino acid in question. The numbering of the amino acid position always refers to SEQ ID 24.*

| Mutant | Mutation | $T_{50}$ [° C.] |
|---|---|---|
| PhV-073 | S1— D2— T3Q A4G P5A A6D G7K F8M Q9K K12R D33N K76I N78T Q109N V123A E144A G152T G217S I300L | 83 |
| PhV-074 | S1— D2— T3Q A4G P5A A6D G7K F8M Q9K K12R D33N K76I N78T Q109N V123A E144A G152T G217S I300L D398E | 83 |
| PhV-075 | S1— D2— T3Q A4G P5A A6D G7K F8M Q9K K12R D33N K76N N78T Q109N V123A G152T I300L | 83 |
| PhV-076 | S1— D2— T3Q A4G P5A A6D G7K F8M Q9K K12R D33N K76N N78T N92A E144A G152T G217S I300L | 84 |
| PhV-077 | S1— D2— T3Q A4G P5A A6D G7K F8M Q9K K12R D33N K76N N78T N92E E144A G152T G217S I300L | 83 |
| PhV-078 | S1— D2— T3Q A4G P5A A6D G7K F8M Q9K K12R D33N K76N N78T N92T E144A G152T G217S I300L | 84 |
| PhV-079 | S1— D2— T3Q A4G P5A A6D G7K F8M Q9K K12R D33N K76N N78T N92V E144A G152T G217S I300L | 83 |
| PhV-080 | S1— D2— T3Q A4G P5A A6D G7K F8M Q9K K12R D33N K76N N78T V123A S136K Q141K E144A G152T G217S I300L | 81 |
| PhV-081 | D2E A4E A6S F8Y D33M K76N N78T E144A G217S D398E | 84 |
| PhV-082 | D2E A4E A6S F8Y D33M K76N N78T V123A E144A T156G G217S Q276N D398E | 82 |
| PhV-083 | D2E A4E A6S F8Y D33M K76N N78T V123A E144A G217S Q276N I300L D398E | 83 |
| PhV-084 | S1— D2— T3Q A4G P5A A6D G7K F8M Q9K K12R D33N K76N N78T N92A V123A S136K E144A G152T G217S | 83 |
| PhV-085 | S1— D2— T3Q A4G P5A A6D G7K F8M Q9K K12R D33N K76I N78T N92A Q109N V123A E144A G152T G217S I300L | 84 |
| PhV-086 | S1— D2— T3Q A4G P5A A6D G7K F8M Q9K K12R D33N K76N N78T Q109N E144A G152T G217S K268A Q276N I300L N346G | 82 |
| PhV-087 | S1— D2— T3Q A4G P5A A6D G7K F8M Q9K K12R D33N K76N N78T V123A E144A G152T E155N G217S | 82 |
| PhV-088 | D2E A4E A6S F8Y D33M K76N N78T V123A E144A T156G G217S D398E | 83 |
| PhV-089 | D2E A4E A6S F8Y D33M K76N N78T V123A E144A G217S I300L D398E | 83 |
| PhV-090 | S1— D2— T3Q A4G P5A A6D G7K F8M Q9K K12R D33N K76N N78T V123A E144A G152T E155H G217S | 82 |
| PhV-091 | S1— D2— T3Q A4G P5A A6D G7K F8M Q9K K12R D33N K76N N78T V123A E144A G152T E155G G217S D345G | 82 |
| PhV-092 | S1— D2— T3Q A4G P5A A6D G7K F8M Q9K K12R D33N K76N N78T V123A E144A G152T E155N G217S D345G | 82 |
| PhV-093 | S1— D2— T3Q A4G P5A A6D G7K F8M Q9K K12R D33N K76N N78T V123A E144A G152T E155H G217S D345M | 82 |
| PhV-094 | S1— D2— T3Q A4G P5A A6D G7K F8M Q9K K12R D33M K76N N78T Q109N E144A T156G G217S Q276N I300L N346G | 83 |
| PhV-095 | S1— D2— T3Q A4G P5A A6D G7K F8M Q9K K12R D33N K76I N78T V123A D398E | 83 |
| PhV-096 | S1— D2— T3Q A4G P5A A6D G7K F8M Q9K K12R D33N K76I N78T N92A E144A G152T G217S | 84 |
| PhV-097 | S1— D2— T3Q A4G P5A A6D G7K F8M Q9K K12R D33N K76N N78T N92A Q109N E144A G152T Q159N G217S | 85 |
| PhV-098 | S1— D2— T3Q A4G P5A A6D G7K F8M Q9K K12R D33N K76I N78T N92A V123A S136K E144A G152T G217S | 84 |
| PhV-099 | D2E A4E A6S F8Y K76N N78T V123A E144A G217S | 84 |
| PhV-100 | K76N N78T V123A E144A G152T G217S N258D H261S Q270N | 82 |
| PhV-101 | K76N N78T V123A E144A G217S N258D H261S Q270N | 83 |
| PhV-102 | D33M K76N N78T V123A E144A G152T G217S N258D H261S Q270N | 82 |
| PhV-103 | V123A E144A G217S | 84 |
| PhV-104 | D33M K76N N78T V123A E144A G217S | 84 |
| PhV-105 | T121Q V123A E144A G152T G217S | 83 |
| PhV-106 | K76N N78T V123A E144A G217S Q270N | 83 |
| PhV-107 | K76N N78T V123A E144A G152T G217S | 83 |
| PhV-109 | Q159N G217S | 83 |
| PhV-110 | V123A E144A Q159N M260I | 84 |
| PhV-111 | N92A V123A E144A Q159N M260I | 85 |
| PhV-112 | S1— D2— T3Q A4G P5A V123A E144A G217S | 84 |
| PhV-113 | S1— D2— T3Q A4G P5A V123A E144A G217S | 84 |
| PhV-114 | A6D G7K F8M Q9K V123A E144A G217S | 84 |
| PhV-115 | N92A Q159N M260I | 85 |
| PhV-116 | Q159N M260I | 84 |
| PhV-117 | S1A D2S T3R A4N V123A E144A G217S | 84 |
| PhV-118 | M260I | 84 |

TABLE 1-continued

Thermostability ($T_{50}$) of the phytase HF598 (see FIG. 1) and its variants in ° C. Changes over SEQ ID 24 are specified at individual amino acid exchanges in the form [original amino acid][position4][new amino acid]. The symbol "—" indicates a deletion of the amino acid in question. The numbering of the amino acid position always refers to SEQ ID 24.

| Mutant | Mutation | $T_{50}$ [° C.] |
|---|---|---|
| PhV-119 | V123A E144A Q159N M260I | 84 |
| PhV-120 | D2E A4E A6S F8Y D33M K76N N78T V123A E144A G217S | 84 |
| PhV-121 | S1— D2— T3Q A4G P5A A6D G7K F8M Q9K K12R D33M K76N N78T V123A E144A G217S | 84 |
| PhV-122 | D33M K76N N78T V123A E144A G217S | 84 |
| PhV-123 | D2E A4E A6S F8Y T121Q V123A E144A G152T G217S N258D H261S Q270N | 82 |
| PhV-124 | D2E A4E A6S F8Y K76N N78T V123A E144A G217S Q270N | 85 |
| PhV-125 | N92A E144A G217S | 84 |
| PhV-126 | N92A E144A G217S M260I | 84 |
| PhV-127 | V123A Q159N M260I | 84 |
| PhV-128 | A4E A6S V123A E144A G217S | 84 |
| PhV-129 | R67L V123A Q159N M260I | 84 |
| PhV-130 | L16V V123A Q159N M260I | 83 |
| PhV-131 | K12R V123A Q159N M260I | 84 |
| PhV-132 | K12R L16V V123A E144A Q159N M260I | 83 |
| PhV-133 | R67L E144A Q159N M260I | 85 |
| PhV-134 | V123A Q159N A166E M260I | 85 |
| PhV-135 | R67L Q159N A166E M260I | 84 |
| PhV-136 | N92A Q159N A166E M260I | 84 |
| PhV-137 | N92A V123A E144A Q159N A166E M260I D398E | 83 |
| PhV-138 | Q159N A166E M260I D398E | 84 |
| PhV-139 | V123A Q159N | 84 |
| PhV-140 | K12R R67L | 84 |
| PhV-141 | L16V R67L | 84 |
| PhV-142 | R67L A166E | 84 |
| PhV-143 | A166E I300L | 84 |
| PhV-144 | I120L I300L | 84 |
| PhV-145 | I120L L371A | 84 |
| PhV-146 | R67L I120L A166E L371A | 84 |
| PhV-147 | I120L I300L L371A | 84 |

Determination of the pH Profile

To determine the pH profile, a modified reaction buffer (100 mM Na acetate, 100 mM glycine, 100 mM imidazole, 1 mM $CaCl_2$, 0.01% Tween 20), which is brought to pH values in the range of from pH 1.5-7 using dilute hydrochloric acid, is used for the phytase assay. To determine the relative activity, the activity measured at pH 5.5 is set at 100%. The results are shown in Tables 2 and 3.

Figure 2:
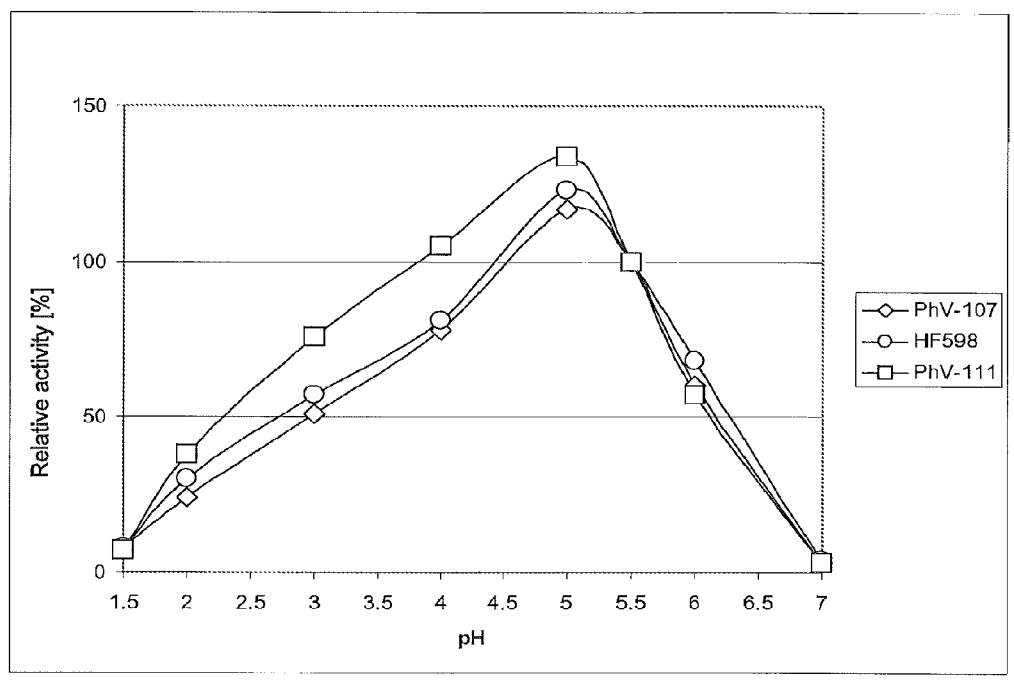
FIGS. 2 A and B show the pH profiles of the phytase HF598 (SEQ ID 24) and some variants thereof. The phytase activity is determined at the respective pH specified. To determine the relative activity data, the activity determined at pH 5.5 is set at 100%. A) The phytases are expressed in *A. niger* and measured from the culture supernatant. B) The phytases are expressed in *E. coli*, concentrated using an Ni-NtA column and then measured.
Figure 2:
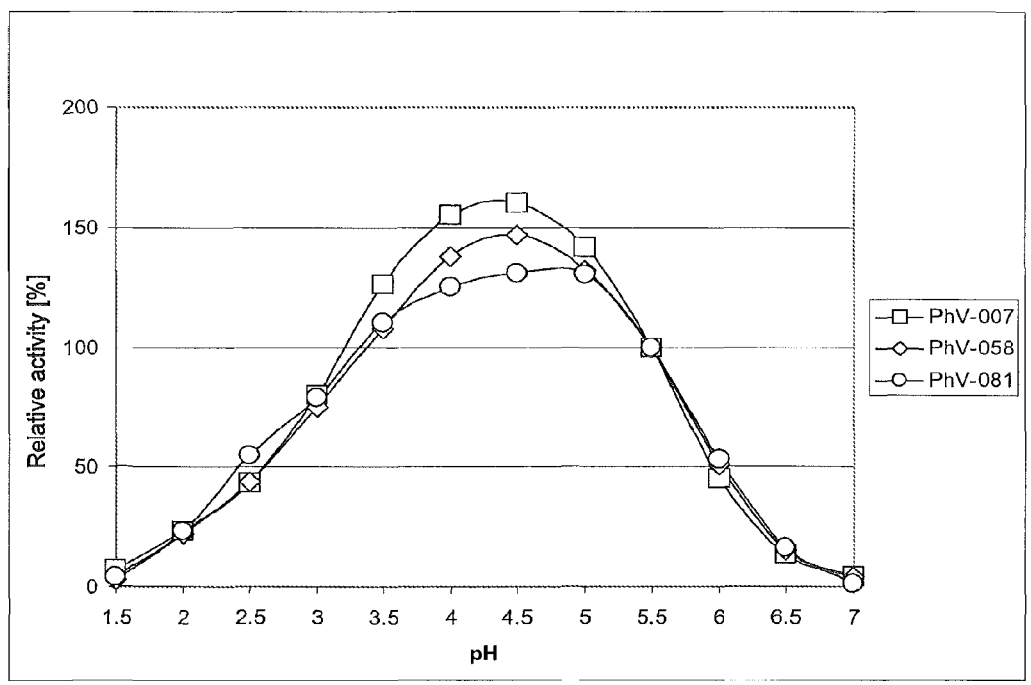
Figure 3:
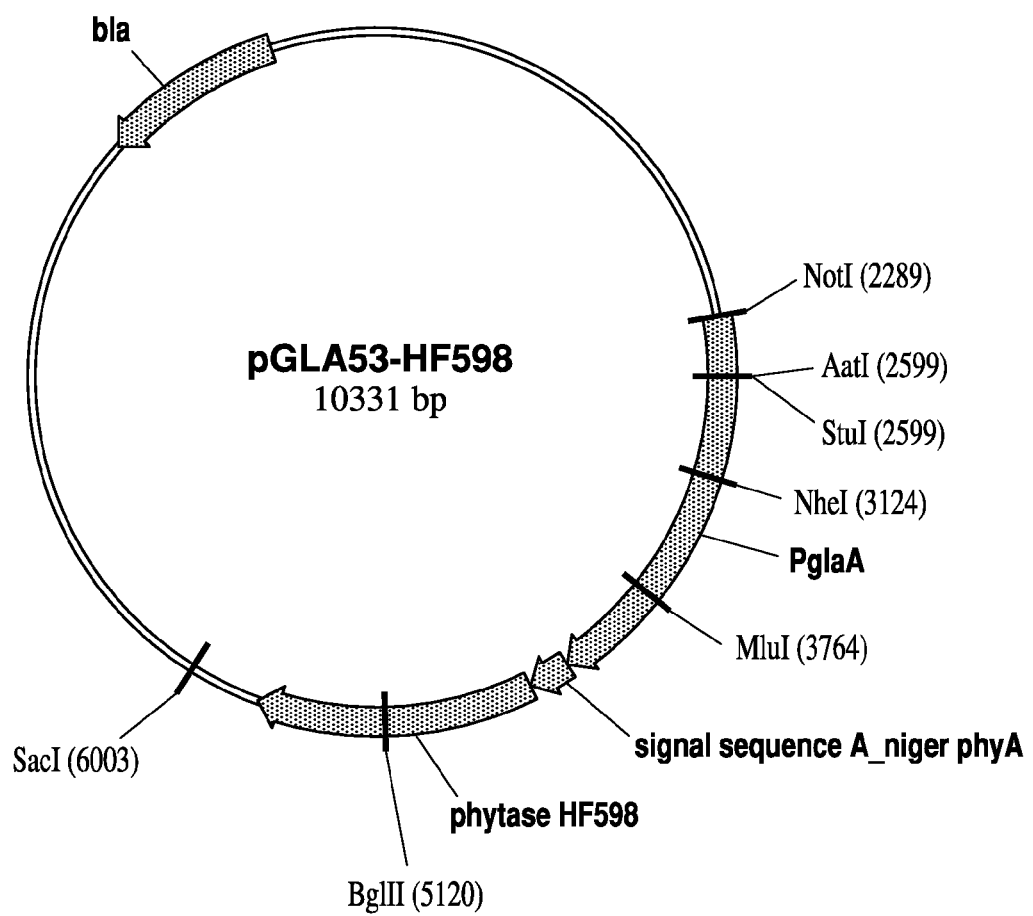
FIG. 3 shows the plasmid map of the expression plasmid pGLA53-HF598.
Figure 4:
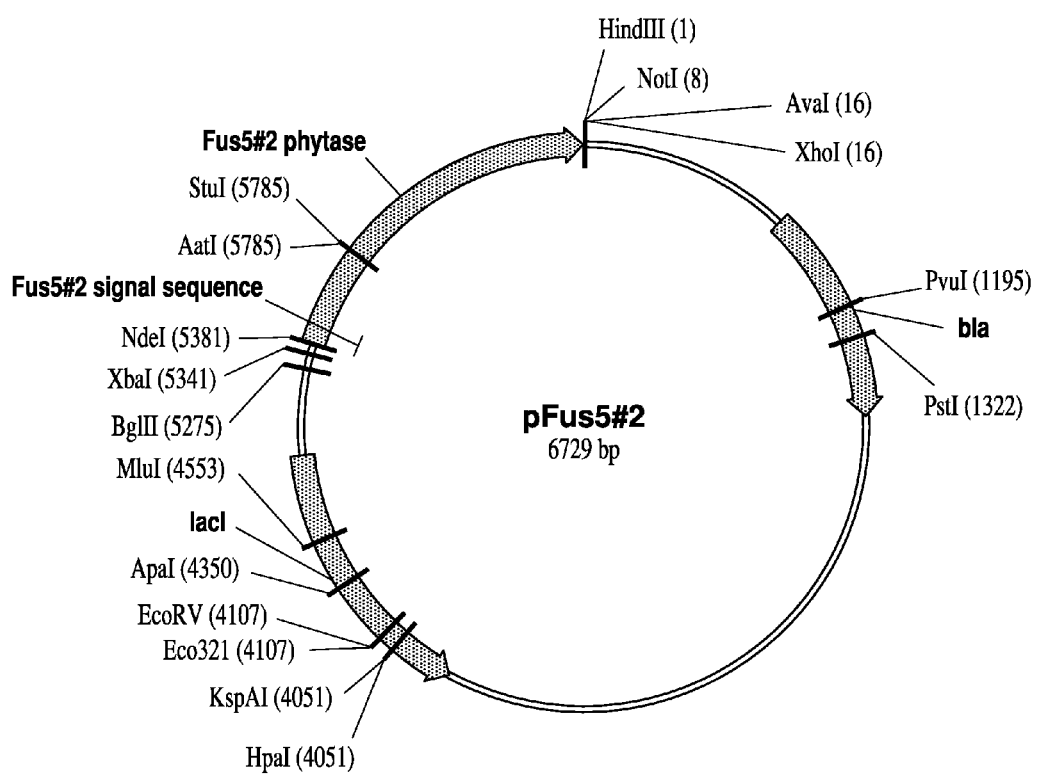
FIG. 4 shows the plasmid map of the expression plasmid pFus5#2.
Figure 5:
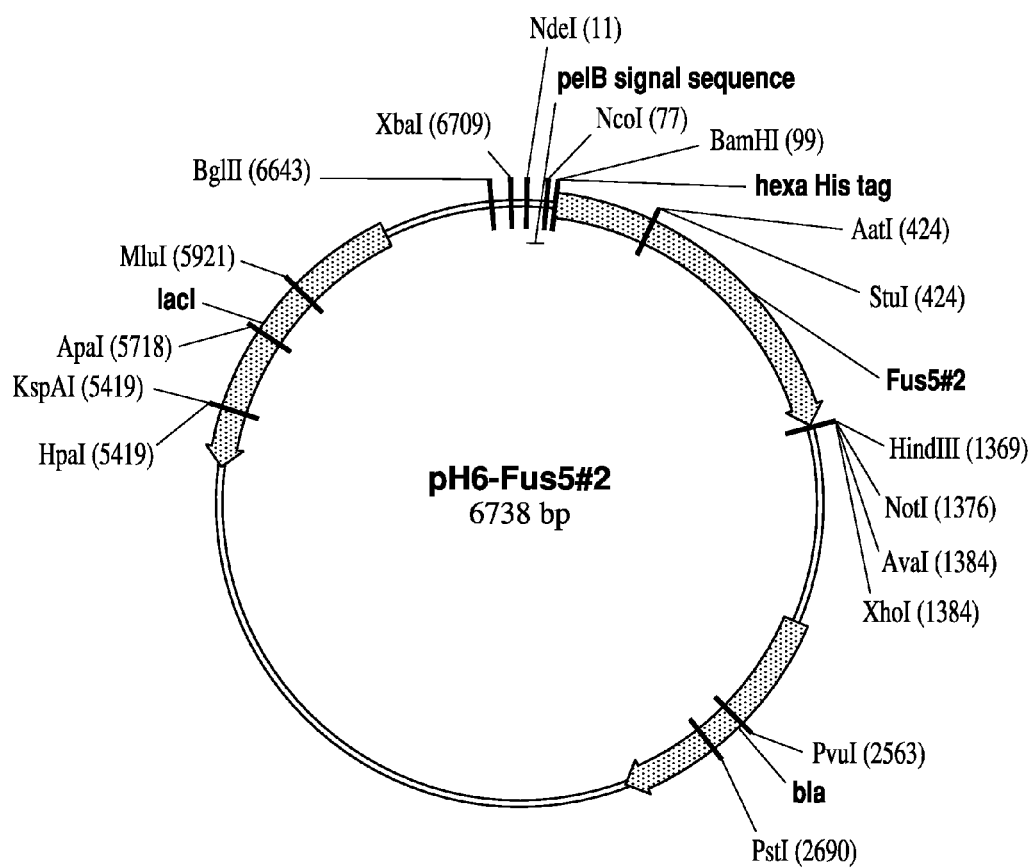
FIG. 5 shows the plasmid map of the expression plasmid pH6-Fus5#2.
Figure 6:
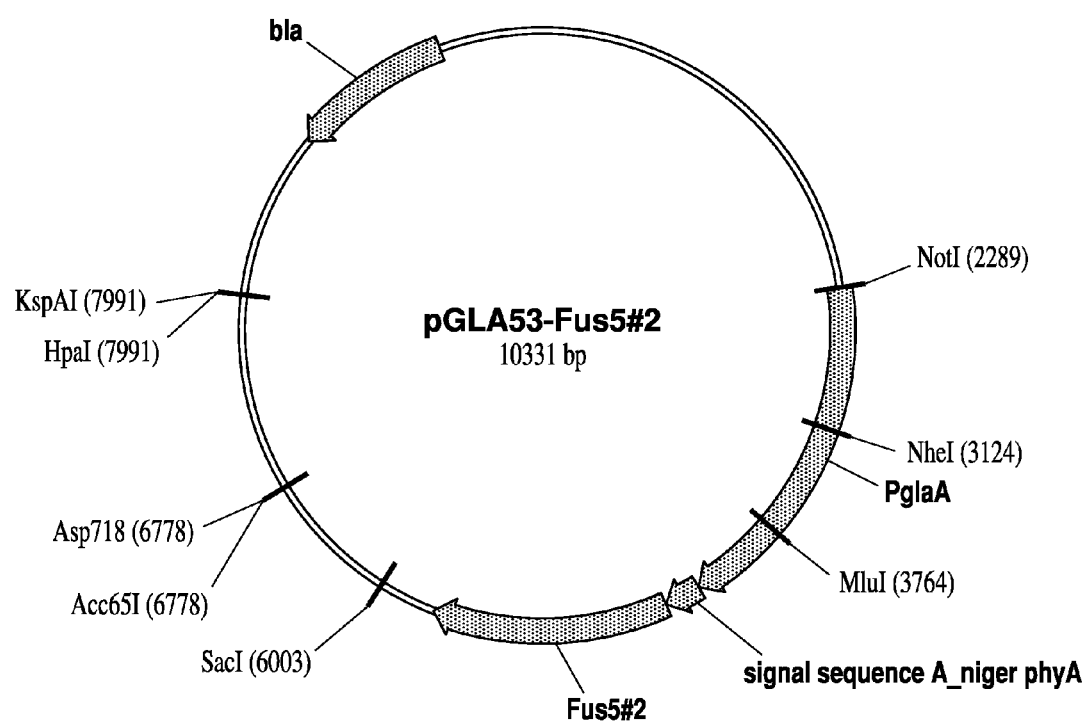
FIG. 6 shows the plasmid map of the expression plasmid pGLA53-Fus5#2.

TABLE 2 pH profiles of the phytase HF598 and its variants. The phytase is expressed in *A. niger* and measured directly from the culture supernatant. The phytase activity is shown in % as a relative value of the activity determined at pH 5.5 (see FIG. 2A).

| pH | 1.5 | 2 | 3 | 4 | 5.0 | 5.5 | 6 | 7.0 |
|---|---|---|---|---|---|---|---|---|
| HF598 | 8 | 30 | 57 | 81 | 123 | 100 | 68 | 4 |
| PhV-107 | 8 | 24 | 51 | 78 | 117 | 100 | 60 | 3 |
| PhV-109 | 6 | 24 | 49 | 76 | 127 | 100 | 59 | 3 |
| PhV-110 | 6 | 27 | 48 | 85 | 134 | 100 | 70 | 4 |
| PhV-111 | 7 | 38 | 76 | 105 | 134 | 100 | 57 | 3 |
| PhV-124 | 7 | 41 | 61 | 76 | 125 | 100 | 67 | 4 |

TABLE 3 pH profiles of some phytase variants. The phytase is expressed in *E. coli* and purified via Ni affinity chromatography. The phytase activity is shown in % as a relative value of the activity determined at pH 5.5 (see FIG. 2B).

| pH | 1.5 | 2 | 2.5 | 3 | 3.5 | 4 | 4.5 | 5 | 5.5 | 6 | 6.5 | 7 |
|---|---|---|---|---|---|---|---|---|---|---|---|---|
| PhV-007 | 7 | 23 | 43 | 80 | 126 | 155 | 160 | 142 | 100 | 45 | 13 | 4 |
| PhV-058 | 3 | 22 | 44 | 75 | 108 | 138 | 147 | 132 | 100 | 51 | 15 | 4 |
| PhV-067 | 6 | 32 | 70 | 123 | 171 | 201 | 182 | 158 | 100 | 52 | 17 | 5 |
| PhV-071 | 4 | 23 | 44 | 77 | 119 | 151 | 157 | 143 | 100 | 53 | 16 | 4 |
| PhV-081 | 4 | 23 | 55 | 79 | 110 | 125 | 131 | 130 | 100 | 53 | 16 | 1 |

Determination of the Stability at pH 2

To determine the stability at pH 2, the phytase sample is diluted in buffer (250 mM glycine, 3 mg/ml BSA, pH 2) to 30 U/ml. The sample is incubated for 30 min at 37° C. Thereafter, the sample is diluted directly with reaction buffer (250 mM Na acetate, 1 mM $CaCl_2$, 0.01% Tween 20, pH 5.5) to the optimum measuring range of the phytase activity determination (approx. 0.6 U/ml), and the phytase activity is measured. By way of reference, the sample is incubated in parallel for 30 min at 37° C. in reaction buffer at a concentration of 30 U/ml, and the phytase activity is likewise analyzed. The activities of the pH-stressed samples are standardized to the reference value, which is set as 100% stability. Natuphos® (BASF) is likewise employed in the assay by way of comparison with a commercial phytase.

Determination of the Stability to Pepsin

To determine the stability to pepsin, the phytase sample is diluted to 30 U/ml in pepsin-comprising buffer (250 mM glycine, 3 mg/ml BSA, pH 2, 10 mg/ml pepsin (Sigma P-7000, 445 U/mg). The sample is incubated for 30 min at 37° C. Thereafter, the sample is diluted directly with reaction buffer (250 mM Na acetate, 1 mM $CaCl_2$, 0.01% Tween 20, pH 5.5) to the optimum measuring range of the phytase activity determination (approx. 0.6 U/ml), and the phytase activity is determined. By way of reference, the sample is incubated in parallel for 30 min at 37° C. in reaction buffer pH 5.5 at a concentration of 30 U/ml, and the phytase activity is likewise analyzed. The activities of the pepsin-treated samples are standardized to the reference value, which is set as 100% stability. Natuphos® (Natuphos® 10000L, BASF SE) was likewise employed in the assay by way of comparison with a commercial phytase.

TABLE 4

Determination of the stability at pH 2 of the phytase HF598 and its variants, and of the phytase Fus5#2 and the commercial phytase Natuphos ®. Samples with a stability >90% are marked as "stable". For a better gradual differentiation between the unstable samples, the stabilities measured are indicated in %.

| Phytase | | Stability at pH 2 |
|---|---|---|
| Natuphos ® | | 65% |
| Fus5#2 | SEQ ID 18 | stable |

| Mutant | Mutation | |
|---|---|---|
| HF598 | SEQ ID 24 | stable |
| PhV-056 | D2E A4E A6S F8Y D33M K76N N78T V123A E144A G152T G217S Q276N N346G | stable |
| PhV-057 | S1— D2— T3Q A4G P5A A6D G7K F8M Q9K K12R D33M K76N N78T Q109N V123A E144A G217S Q276N I300L N346G | stable |
| PhV-058 | D2E A4E A6S F8Y D33M K76N N78T V123A E144A G217S | stable |
| PhV-059 | D2E A4E A6S F8Y D33M K76N N78T V123A E144A G217S D398E | stable |
| PhV-067 | S1— D2— T3Q A4G P5A A6D G7K F8M Q9K K12R D33N K76N N78T N92A E144A G152T G217S | stable |
| PhV-071 | S1A D2S T3R A4N P5A A6D G7K F8M Q9K K12R D33N K76N N78T V123A E144A G152T G217S | stable |
| PhV-081 | D2E A4E A6S F8Y D33M K76N N78T E144A G217S D398E | stable |
| PhV-107 | K76N N78T V123A E144A G152T G217S | stable |
| PhV-109 | Q159N G217S | stable |
| PhV-110 | V123A E144A Q159N M260I | stable |
| PhV-111 | N92A V123A E144A Q159N M260I | stable |

TABLE 5

Determination of the stability to pepsin of the phytase HF598 and its variants, and of the phytase Fus5#2 and the commercial phytase Natuphos ®. Samples with a stability >80% are marked as "stable". For a better gradual differentiation between the unstable samples, the stabilities measured are indicated in %.

| Phytase | | Stability to pepsin |
|---|---|---|
| Natuphos ® | | 20% |
| Fus5#2 | SEQ ID 18 | 1% |

| Mutant | Mutation | |
|---|---|---|
| HF598 | SEQ ID 24 | stable |
| PhV-056 | D2E A4E A6S F8Y D33M K76N N78T V123A E144A G152T G217S Q276N N346G | stable |
| PhV-057 | S1— D2— T3Q A4G P5A A6D G7K F8M Q9K K12R D33M K76N N78T Q109N V123A E144A G217S Q276N I300L N346G | stable |
| PhV-058 | D2E A4E A6S F8Y D33M K76N N78T V123A E144A G217S | stable |
| PhV-059 | D2E A4E A6S F8Y D33M K76N N78T V123A E144A G217S D398E | stable |
| PhV-067 | S1— D2— T3Q A4G P5A A6D G7K F8M Q9K K12R D33N K76N N78T N92A E144A G152T G217S | stable |
| PhV-071 | S1A D2S T3R A4N P5A A6D G7K F8M Q9K K12R D33N K76N N78T V123A E144A G152T G217S | stable |
| PhV-081 | D2E A4E A6S F8Y D33M K76N N78T E144A G217S D398E | stable |
| PhV-107 | K76N N78T V123A E144A G152T G217S | stable |
| PhV-109 | Q159N G217S | stable |
| PhV-110 | V123A E144A Q159N M260I | stable |
| PhV-111 | N92A V123A E144A Q159N M260I | stable |

---

We claim:

1. A synthetic phytase which has an amino acid sequence with at least 90% sequence identity to the amino acid sequence of SEQ ID NO: 24.

2. The phytase of claim 1, which has an amino acid sequence having at least, 95%, 96%, 97%, 98%, or 99% sequence identity to the amino acid sequence of SEQ ID NO: 24.

3. The phytase of claim 1, wherein the amino acid sequence has at least one conservative amino acid exchange at least one position compared with the sequence of SEQ ID NO: 24.

4. The phytase of claim 1, which is an isolated phytase.

5. The phytase of claim 1, which has an elevated pepsin stability, an elevated thermostability, and/or an elevated specific activity compared with the two wild-type phytases from *Yersinia mollaretii* and *Hafnia* sp.

6. An animal feed additive comprising the phytase of claim 1 and further feed additives.

7. An animal feed comprising the phytase of claim 1.

8. A method for producing an animal feed, comprising
a) utilizing the phytase of claim 1 in the production of an animal feed; or
b) utilizing an animal feed additive which comprises the phytase of claim 1 and further feed additives in the production of an animal feed.

9. The phytase of claim 1, which comprises an amino acid sequence having at least 95% sequence identity to the amino acid sequence of SEQ ID NO: 24.

10. The phytase of claim 1, which comprises the amino acid sequence of SEQ ID NO: 24.

* * * * *